(12) United States Patent
Jones et al.

(10) Patent No.: US 10,909,216 B2
(45) Date of Patent: Feb. 2, 2021

(54) VIRTUAL MENTAL HEALTH PLATFORM

(71) Applicant: SkyTherapist, Inc., Smyrna, GA (US)

(72) Inventors: Keith Damond Jones, Smyrna, GA (US); Afshan Munnaver Ali, Atlanta, GA (US)

(73) Assignee: SKYTHERAPIST, INC., Smyrna, GA (US)

( * ) Notice: Subject to any disclaimer, the term of this patent is extended or adjusted under 35 U.S.C. 154(b) by 806 days.

(21) Appl. No.: 14/706,464

(22) Filed: May 7, 2015

(65) Prior Publication Data

US 2015/0324532 A1    Nov. 12, 2015

Related U.S. Application Data

(60) Provisional application No. 62/058,860, filed on Oct. 2, 2014, provisional application No. 61/989,631, filed on May 7, 2014, provisional application No. 61/989,579, filed on May 7, 2014, provisional application No. 61/989,610, filed on May 7, 2014.

(51) Int. Cl.
| | |
|---|---|
| *G06F 19/00* | (2018.01) |
| *G16H 40/20* | (2018.01) |
| *G16H 10/20* | (2018.01) |
| *G16H 20/70* | (2018.01) |

(52) U.S. Cl.
CPC ...... *G06F 19/3418* (2013.01); *G06F 19/3481* (2013.01); *G16H 10/20* (2018.01); *G16H 20/70* (2018.01); *G16H 40/20* (2018.01)

(58) Field of Classification Search
CPC . G06F 19/3418; G06F 19/3481; G16H 40/20; G16H 10/20; G16H 20/70
See application file for complete search history.

(56) References Cited

U.S. PATENT DOCUMENTS

| | | | |
|---|---|---|---|
| 2002/0035486 A1* | 3/2002 | Huyn | G06F 19/3418 705/3 |
| 2010/0235184 A1* | 9/2010 | Firminger | G06Q 10/10 705/2 |
| 2014/0288951 A1* | 9/2014 | Zielinski | G06Q 50/22 705/2 |
| 2015/0154721 A1* | 6/2015 | Thompson | G06Q 50/22 705/2 |

OTHER PUBLICATIONS

Aafjes-van Doorn et al., Language Style Matching in Psychotherapy: An Implicit Aspect of Alliance, Jul. 2020, Journal of Counseling Psychology, Abstract. (Year: 2020).*

* cited by examiner

*Primary Examiner* — Christopher L Gilligan
(74) *Attorney, Agent, or Firm* — Morris, Manning & Martin, LLP; Bryan D. Stewart; Adam J. Thompson

(57) ABSTRACT

According to various embodiments, systems and methods herein describe a virtual mental health/therapy platform. In particular embodiments, the systems and methods disclosed herein describe a system that includes matching a particular patient to one or more therapists, providing an initial assessment of the particular patient to the one or more therapists, and providing a continuous care application to the particular patient (e.g., to track process, receive care plan related reminders, and various other functionality).

16 Claims, 21 Drawing Sheets

EXEMPLARY SYSTEM ENVIRONMENT

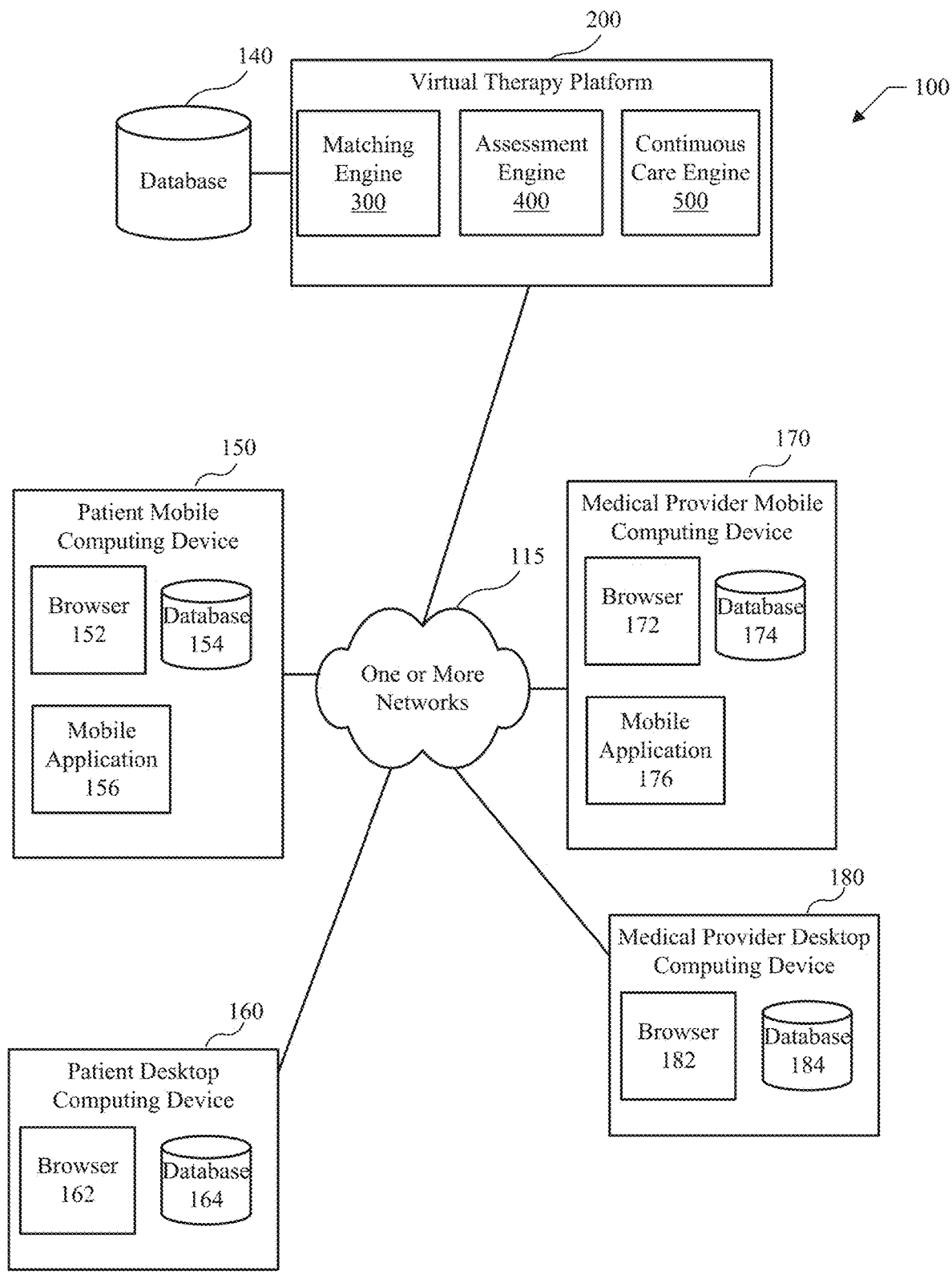
FIG. 1 EXEMPLARY SYSTEM ENVIRONMENT

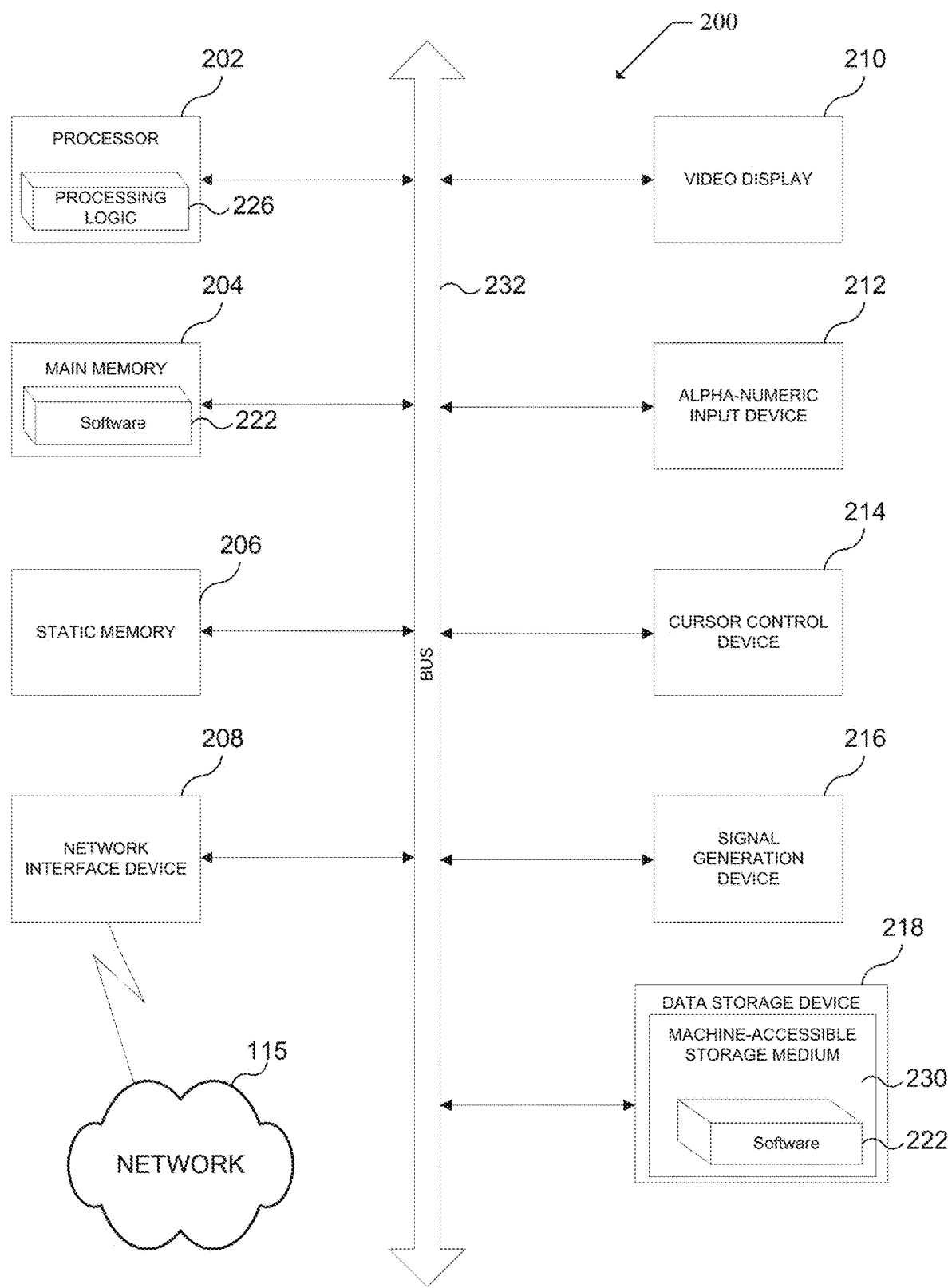
FIG. 2 EXEMPLARY COMPUTER ARCHITECTURE

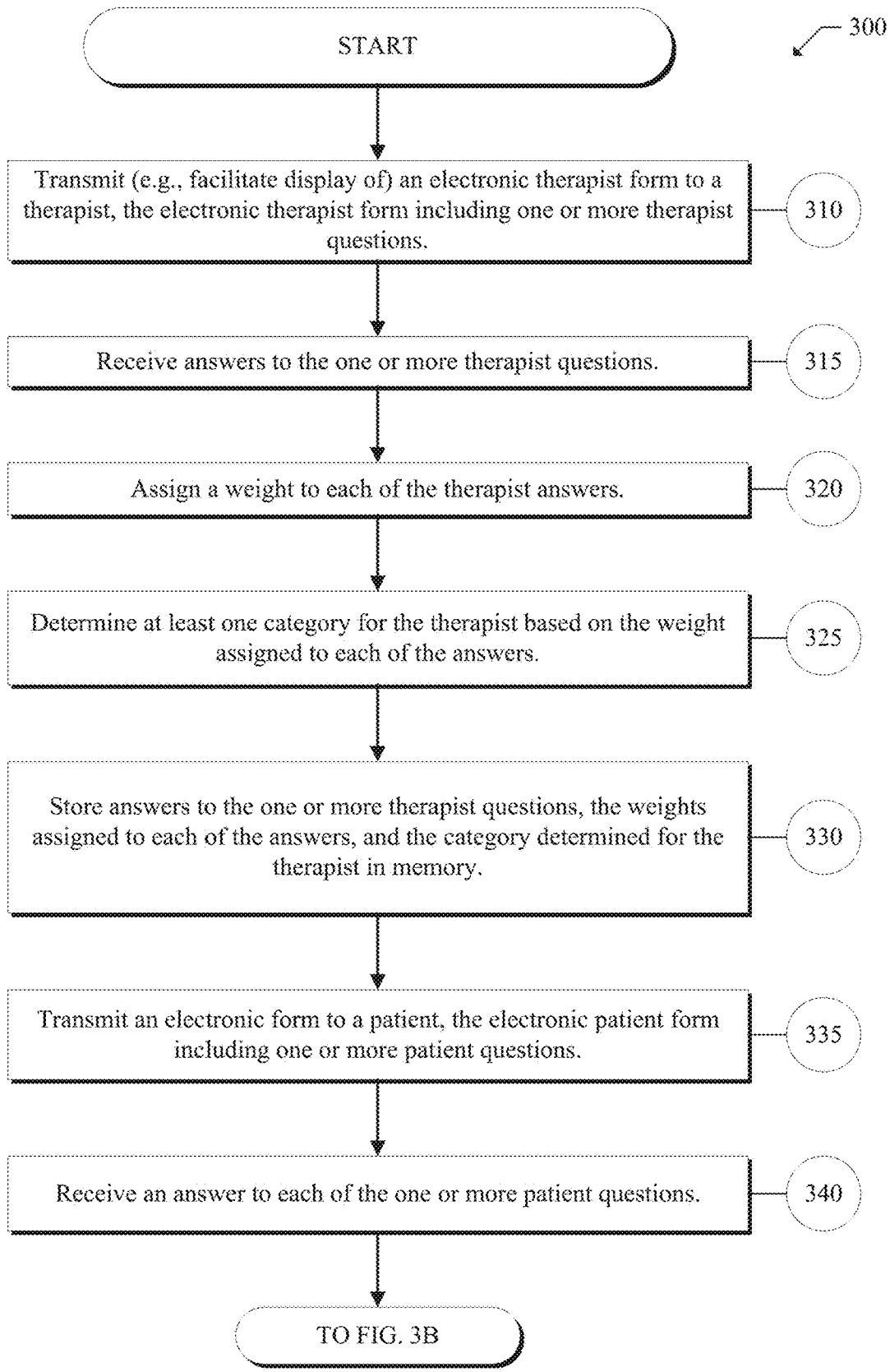
FIG. 3A EXEMPLARY MATCHING PROCESS

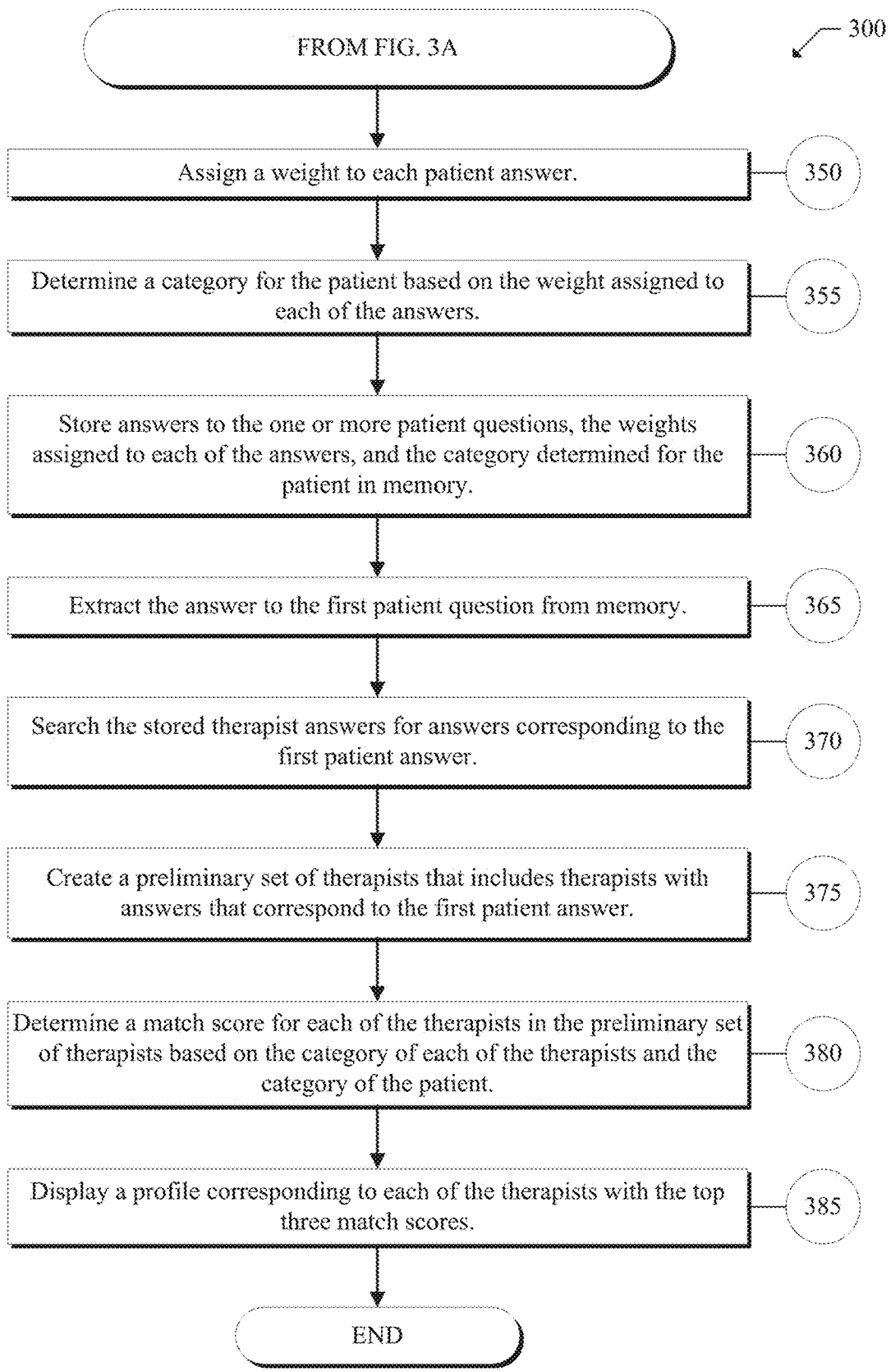
FIG. 3B  EXEMPLARY MATCHING PROCESS

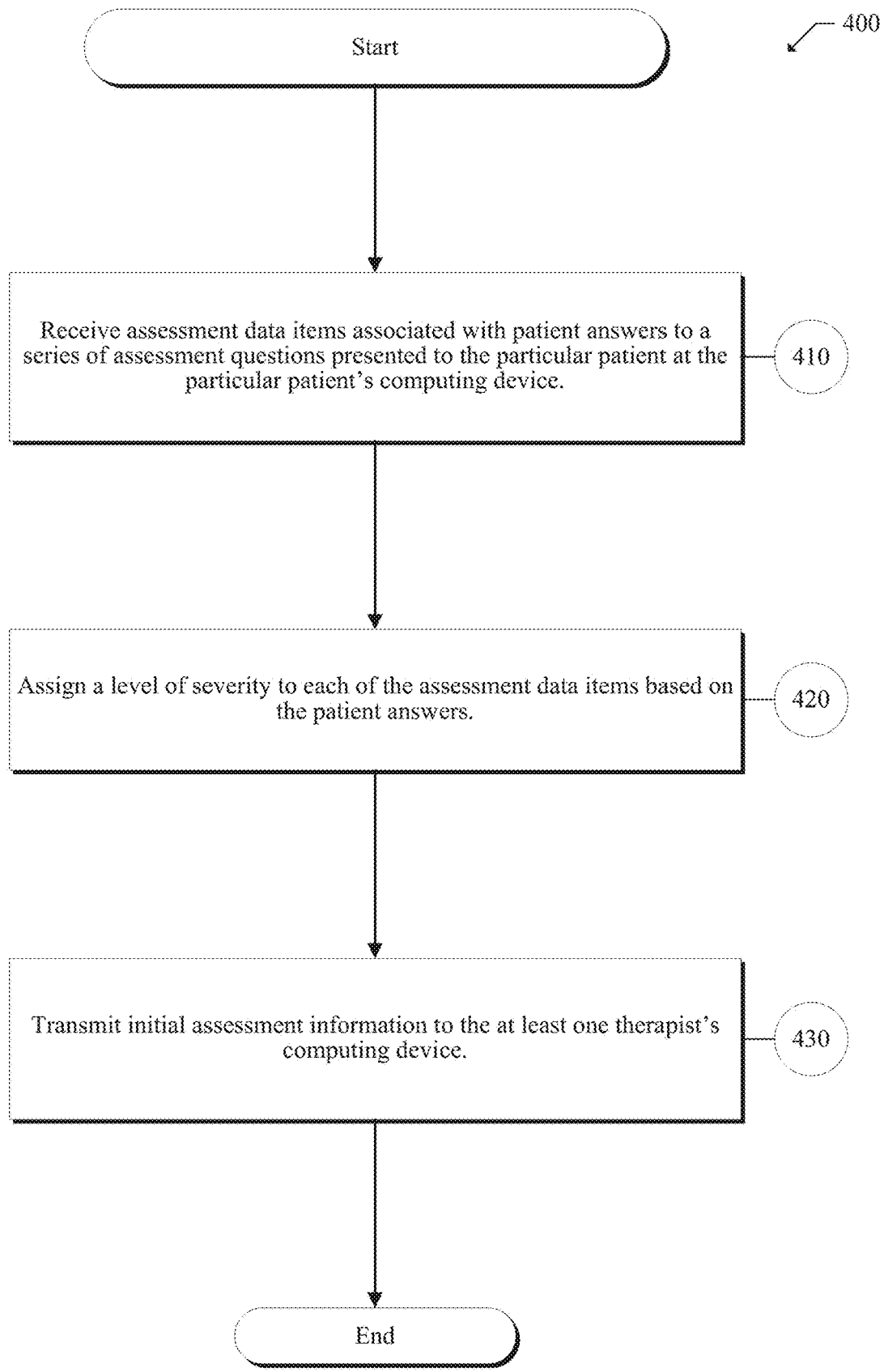
FIG. 4 EXEMPLARY ASSESSMENT PROCESS

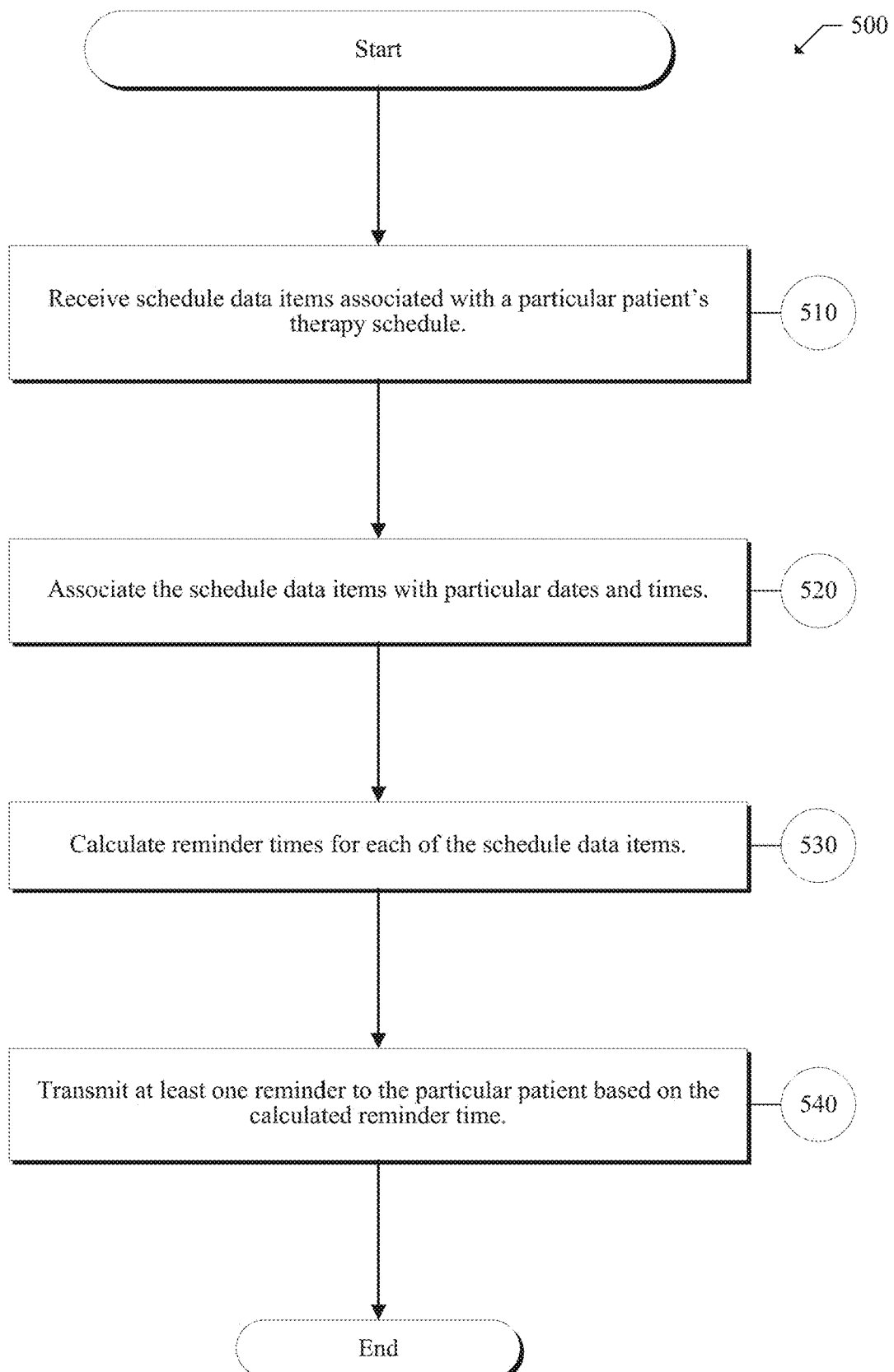
FIG. 5  EXEMPLARY CONTINUOUS CARE PROCESS

FIG. 6 EXEMPLARY MATCHING QUESTIONNAIRE 1

600

616 — My problem involves a loved one, such as a spouse or child who could also benefit from my therapy sessions
618 — 1 2 3 4 5

620 — My therapist must be able to understand my feelings and get me
622 — 1 2 3 4 5

624 — I would like to discuss my dreams with my therapist
626 — 1 2 3 4 5

628 — I am interested in changing a feeling, such as anxiety, or changing a behavior, such as smoking
630 — 1 2 3 4 5

632 — Freedom and self-awareness are very important to me
634 — 1 2 3 4 5

FIG. 7 EXEMPLARY MATCHING QUESTIONNAIRE 2

I would like to discuss my dreams with my therapist — 636, 638

I am interested in changing a feeling, such as anxiety, or changing a behavior, such as smoking — 640, 642

Freedom and self-awareness are very important to me — 644, 646

My problems come from issues outside my control such as my sex, race, ethnicity, education level, or socioeconomic status — 648, 650

Submit Answers — 652

FIG. 8  EXEMPLARY MATCHING QUESTIONNAIRE 3

FIG. 9  EXEMPLARY MATCH RESULTS

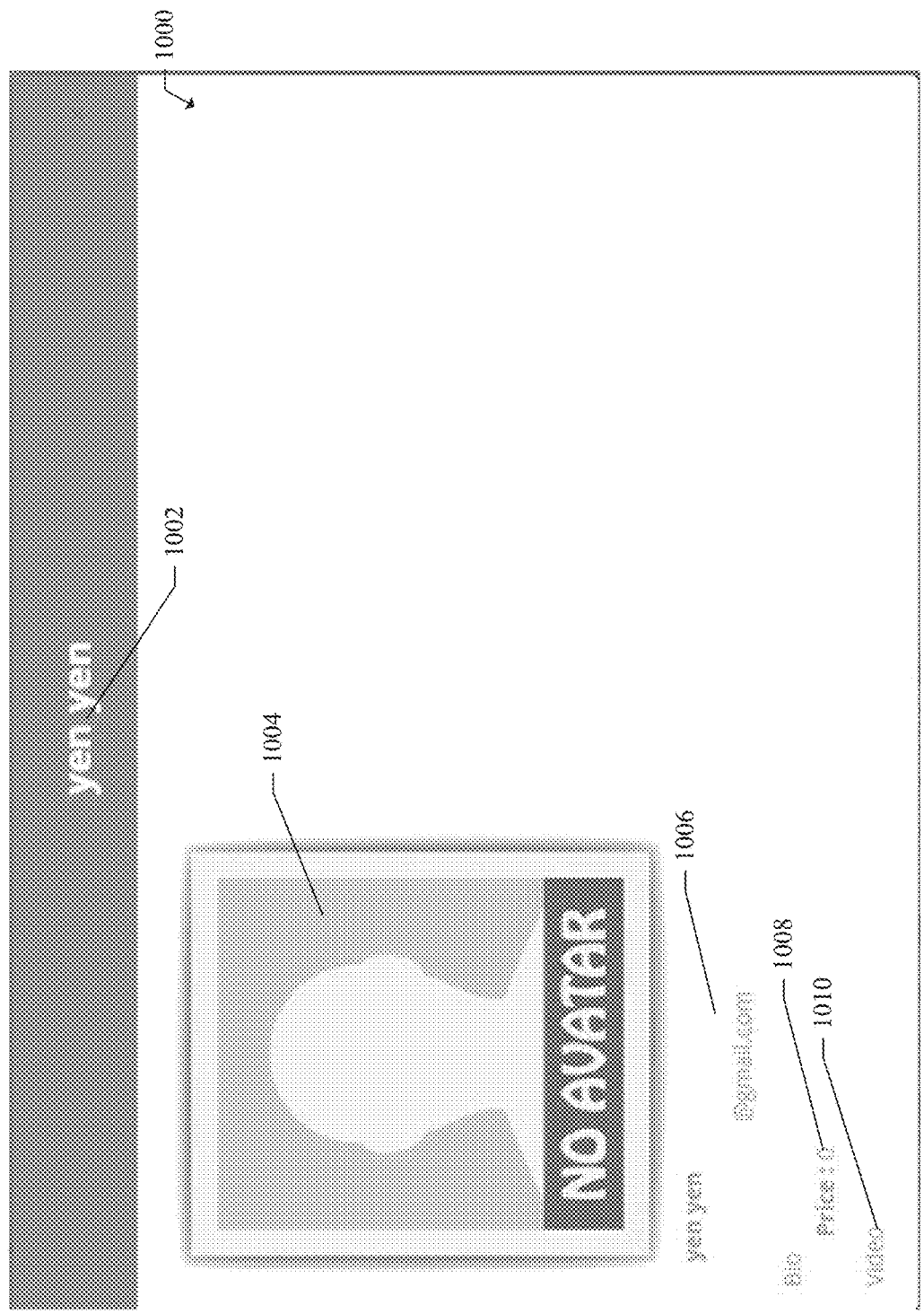
FIG. 10 EXEMPLARY THERAPIST PROFILE

Intake Assesment

INSTRUCTIONS

Please answer the following questions so that you can have a productive session with your SkyTherapist.

QUESTIONS THAT YOU RATE FROM 1-6 — 1102

1 = COMPLETELY AGREE
2 = AGREE
3 = SOMETIMES AGREE
4 = SOMETIMES DISAGREE
5 = DISAGREE
6 = COMPLETELY DISAGREE

Other people's opinions are not important in terms of the whole scheme of life — 1104

False — 1106

Being less than the best at what a person does means that he or she is either lazy or not trying hard enough — 1108

True — 1110

FIG. 11  EXEMPLARY INTAKE ASSESSMENT 1

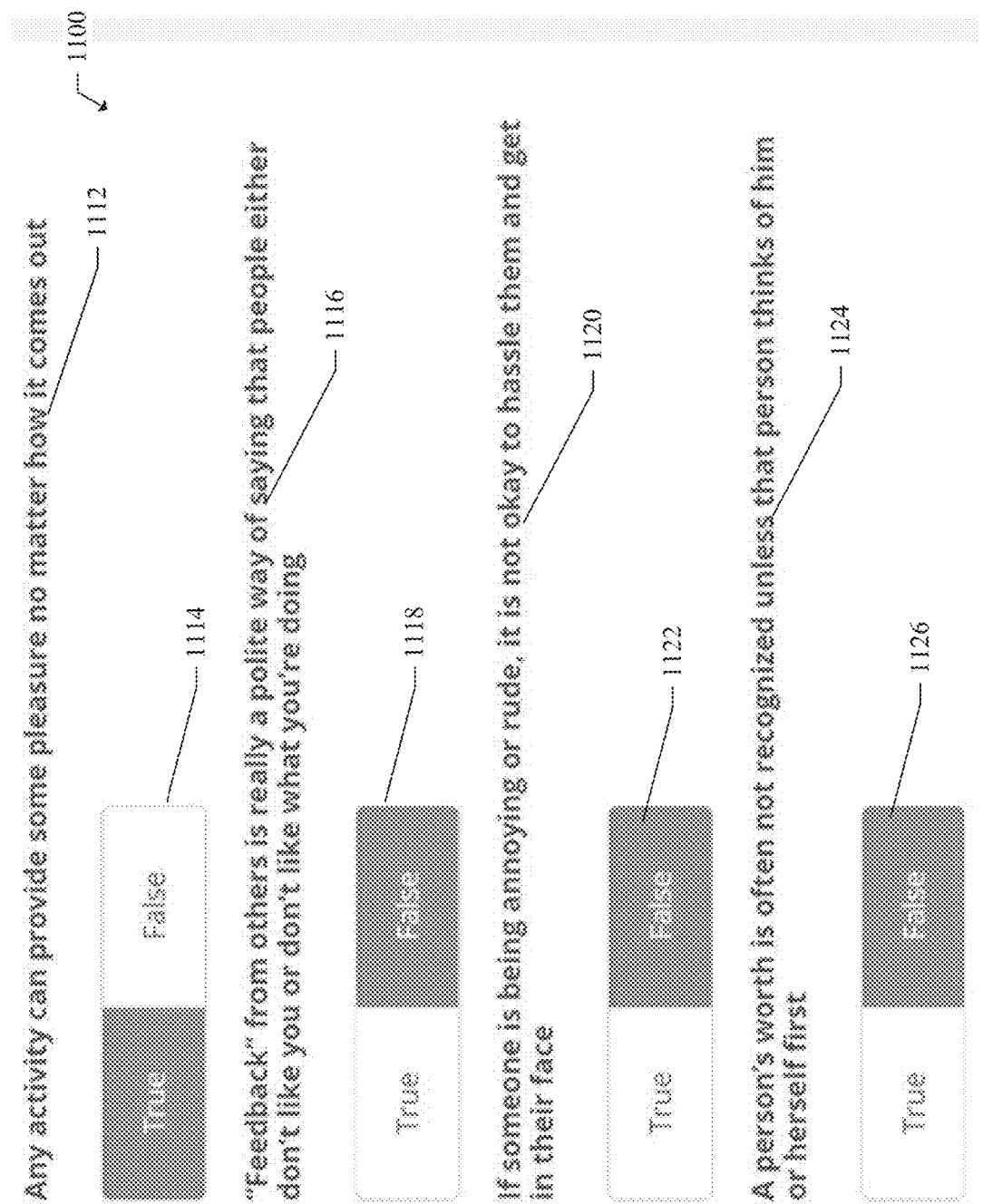
FIG. 12  EXEMPLARY INTAKE ASSESSMENT 2

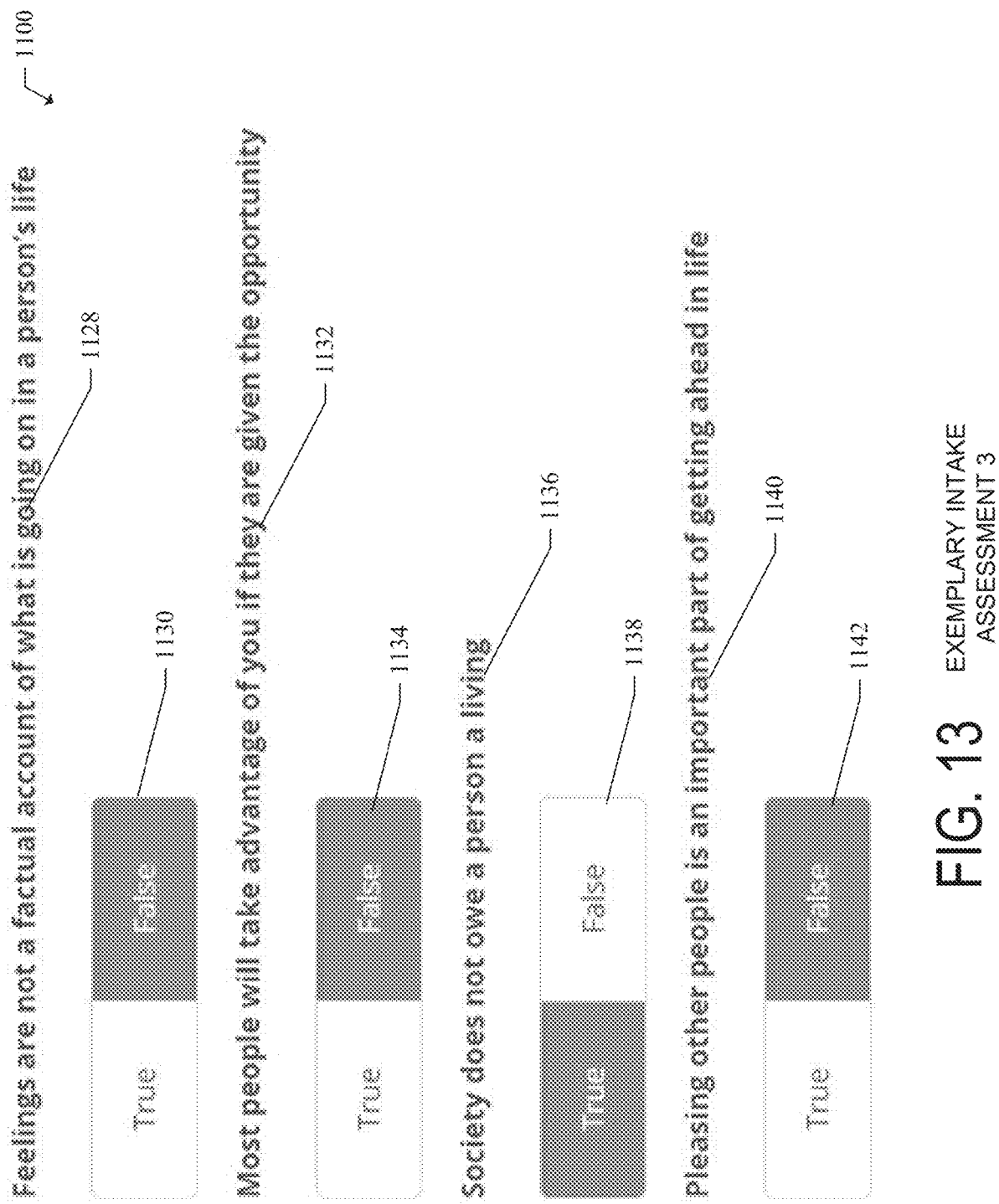
FIG. 13  EXEMPLARY INTAKE ASSESSMENT 3

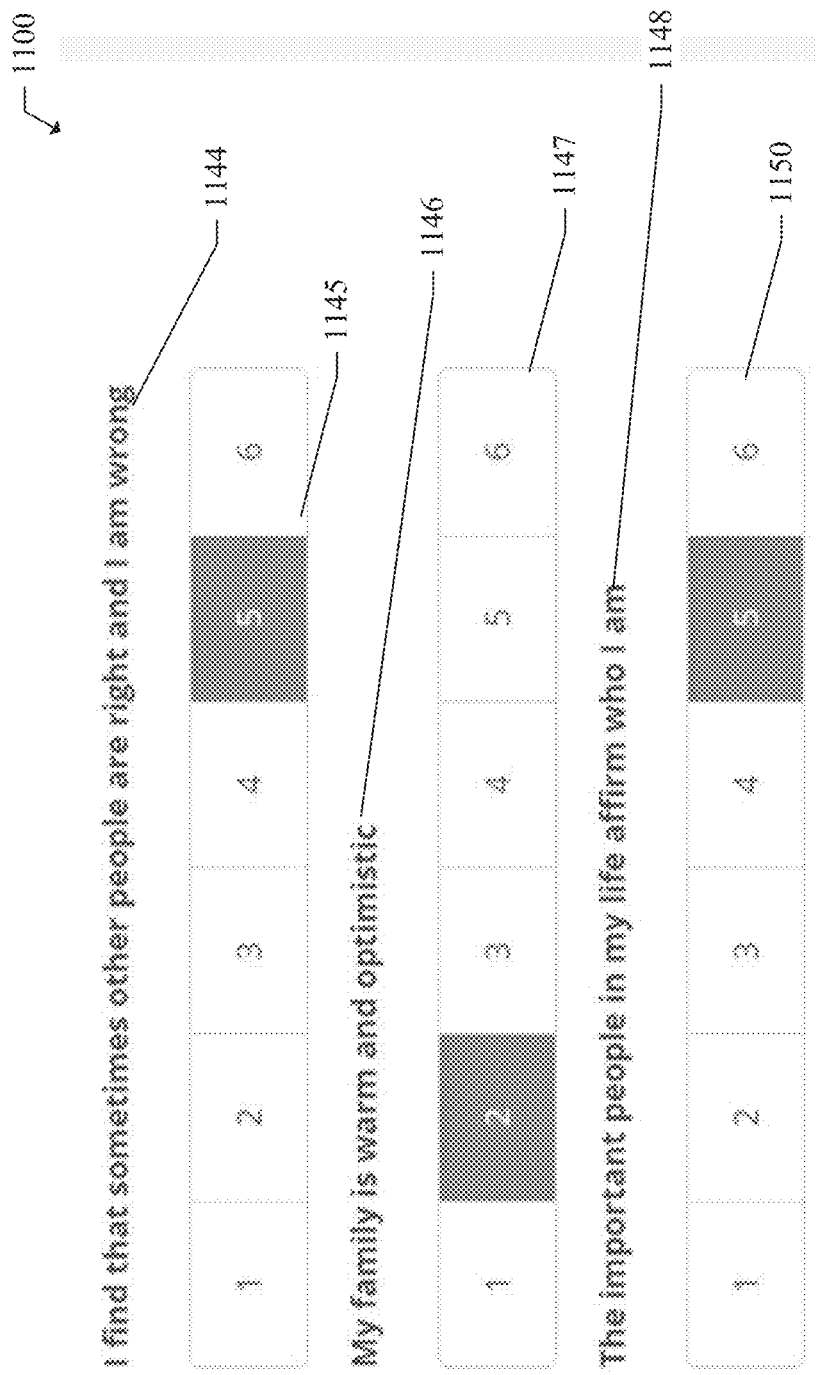
FIG. 14  EXEMPLARY INTAKE ASSESSMENT 4

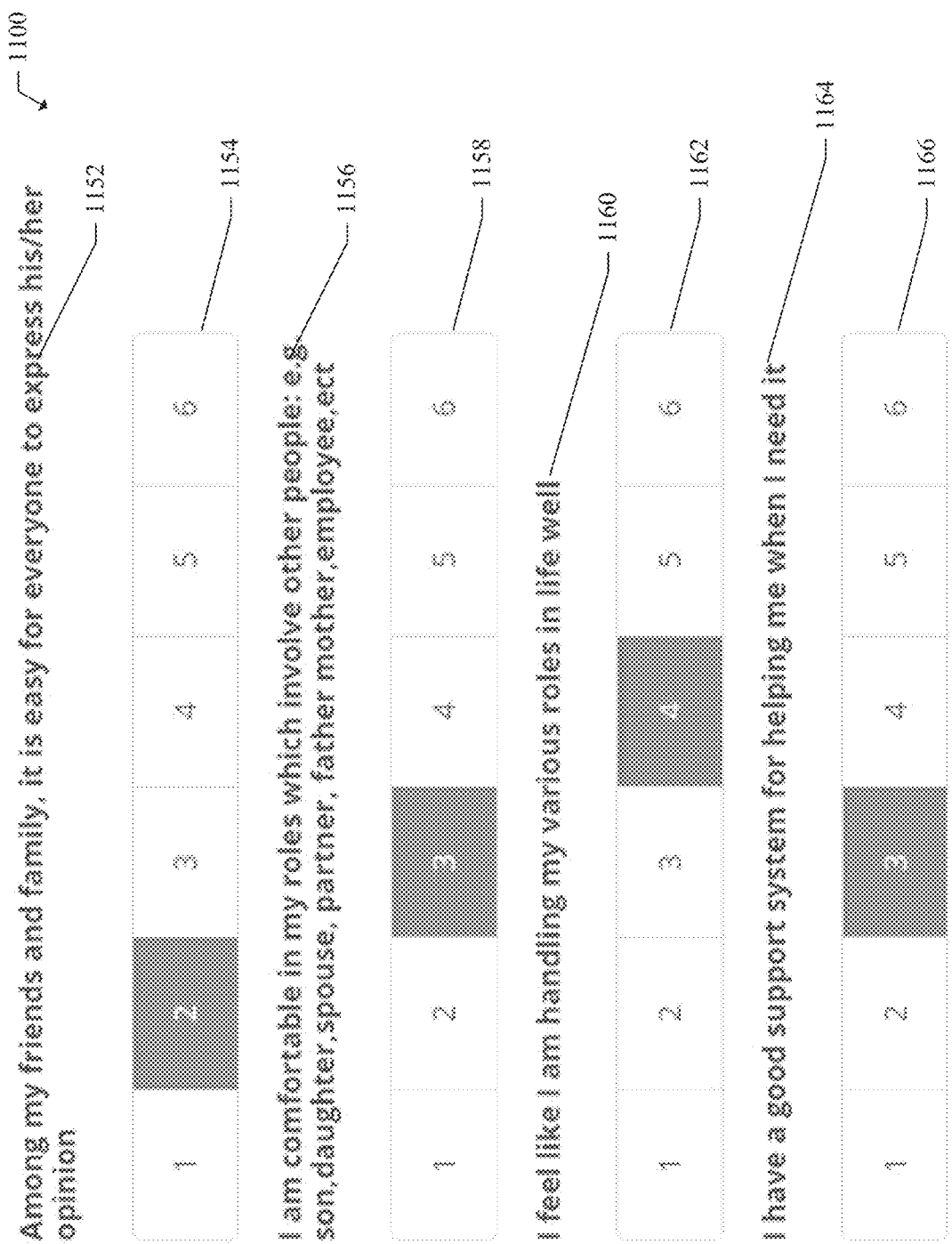
FIG. 15    EXEMPLARY INTAKE ASSESSMENT 5

I am able to keep other people's problems from complicating my life  1168
[1] [2] [3] [4] [5] [6]  1170

I relax without too much effort  1172
[1] [2] [3] [4] [5] [6]  1174

I handle my problems without too much worry  1176
[1] [2] [3] [4] [5] [6]  1178

Please answer all questions before continuing

[Submit Answers]  1180

FIG. 16   EXEMPLARY INTAKE ASSESSMENT 6

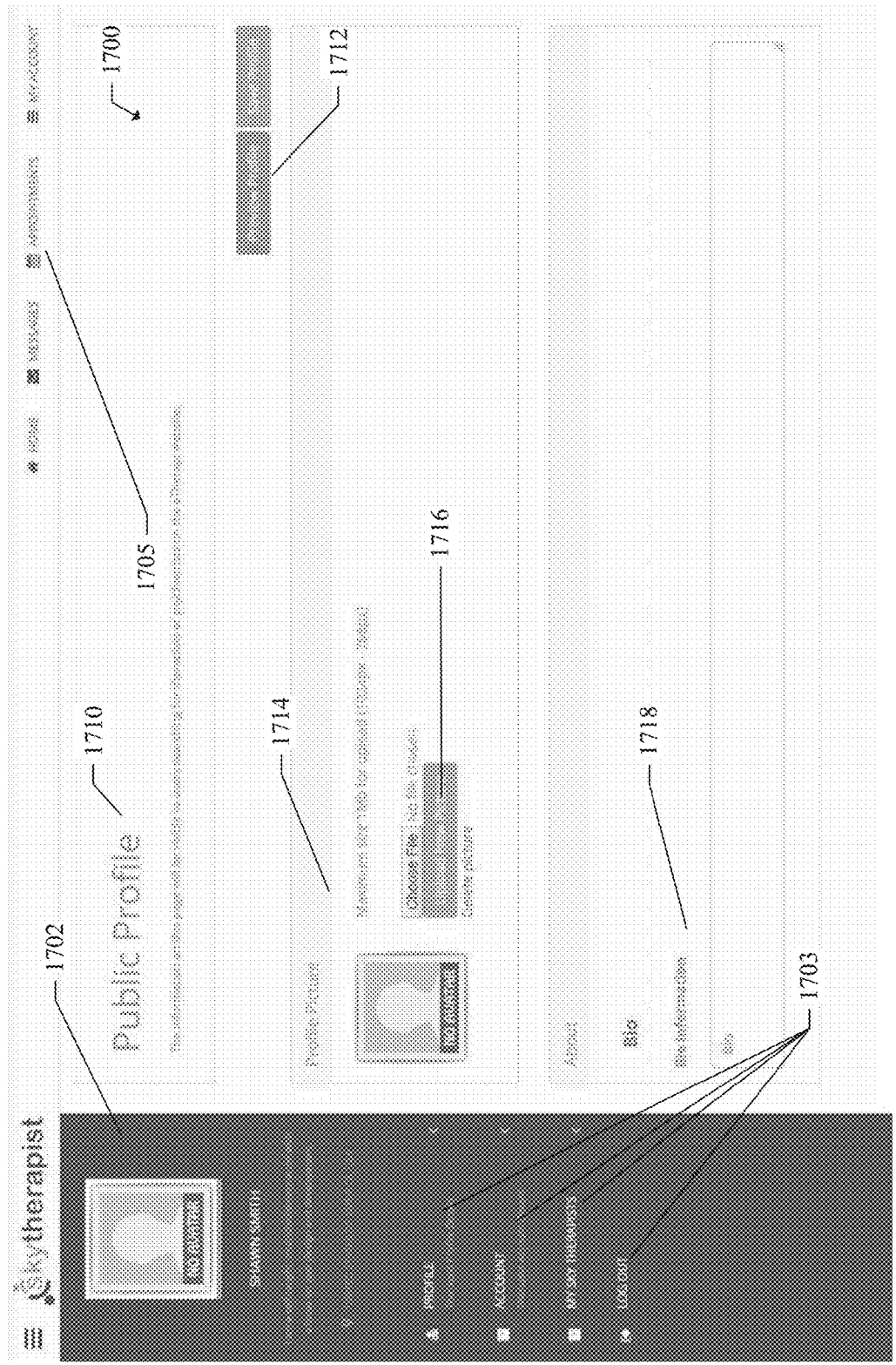
FIG. 17 EXEMPLARY PATIENT PROFILE

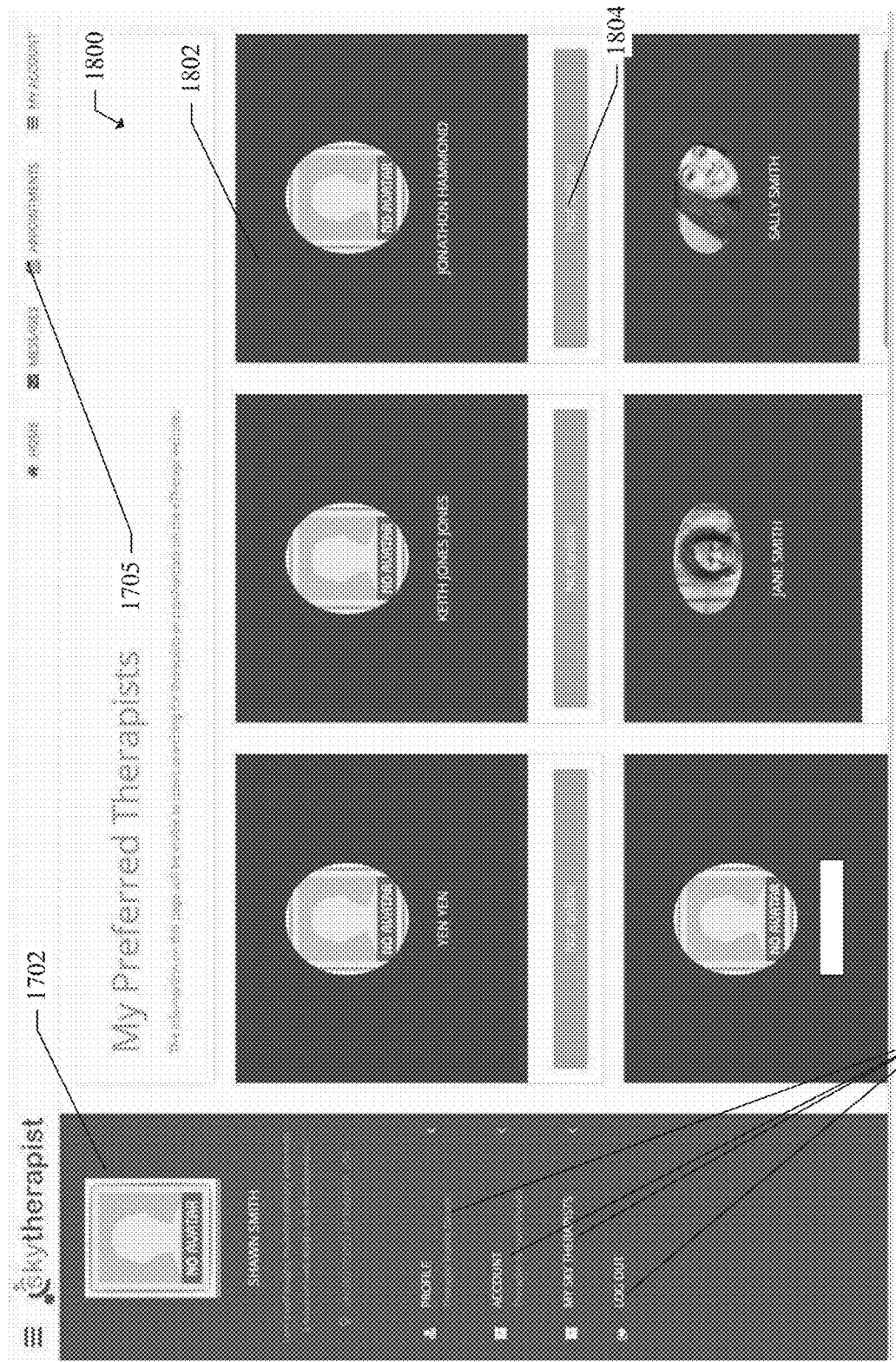
FIG. 18 EXEMPLARY PREFERRED THERAPISTS

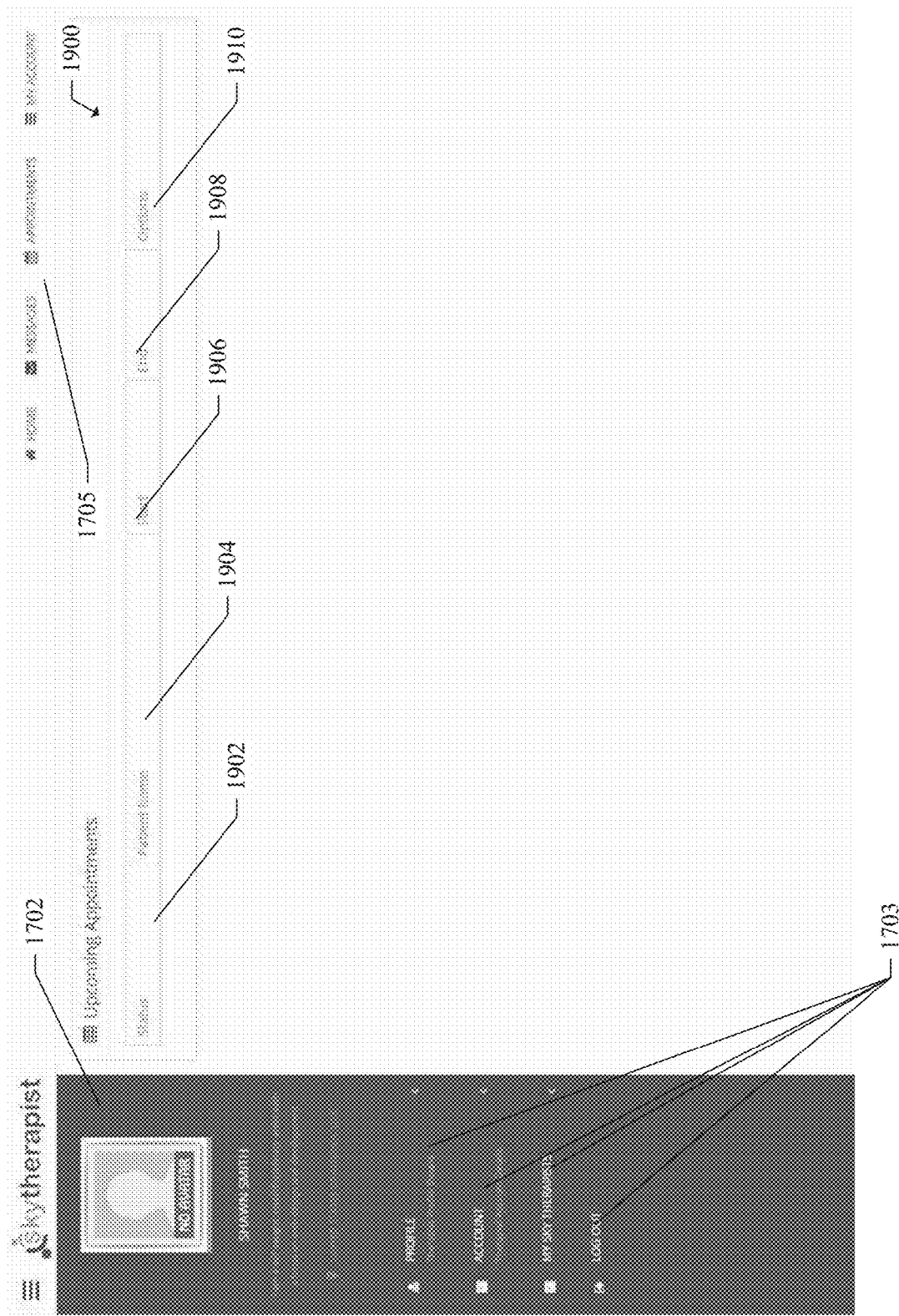
FIG. 19  EXEMPLARY APPOINTMENTS

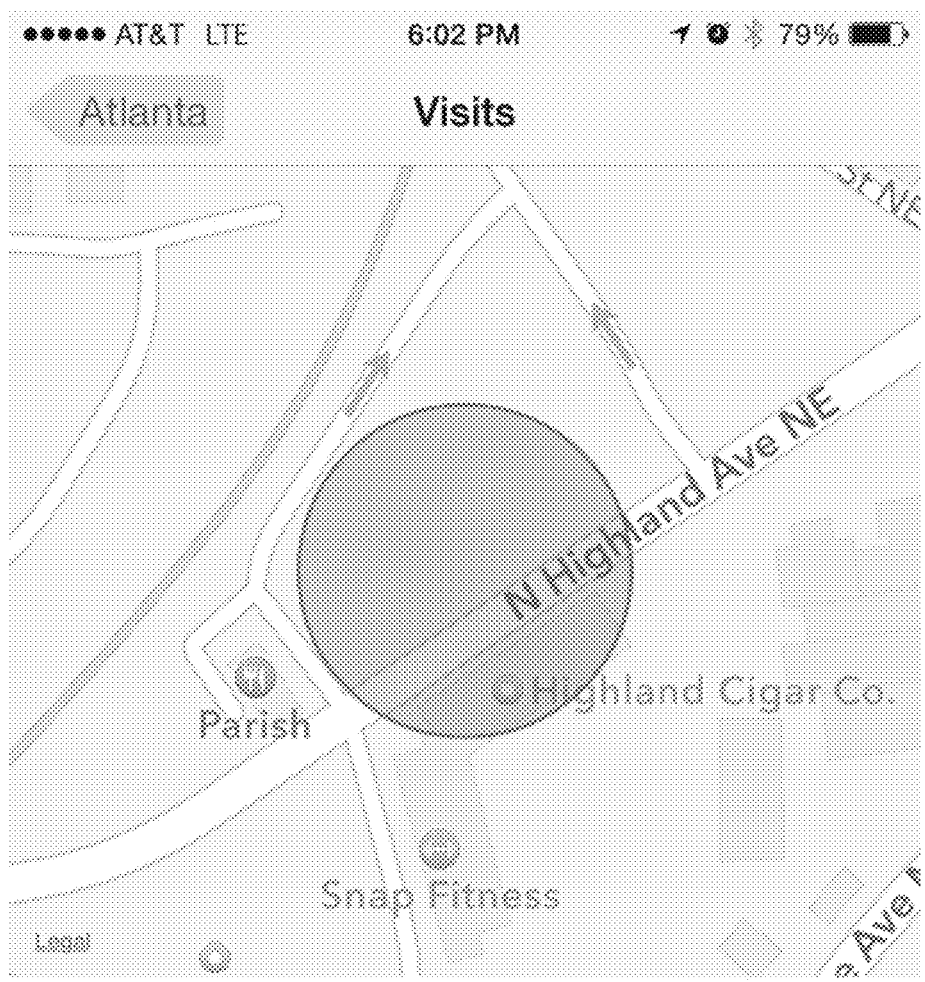
FIG. 20  EXEMPLARY GEOLOCATIONS

VIRTUAL MENTAL HEALTH PLATFORM

CROSS-REFERENCE TO RELATED APPLICATIONS

This application claims the benefit under 35 U.S.C. § 119(e) of U.S. Provisional Patent Application Nos:
62/058,860, filed Oct. 2, 2014, entitled, "SKYTHERAPIST INSTRUMENT WORKFLOW INTEGRATION," incorporated herein by reference in its entirety;
61/989,579, filed May 7, 2014, entitled, "PSYCHOTHERAPIST COMPATIBILITY INSTRUMENT," incorporated herein by reference in its entirety;
61/989,610, filed May 7, 2014, entitled, "PSYCHOTHERAPIST COLOR CODED INTAKE ASSESSMENT INSTRUMENT," incorporated herein by reference in its entirety; and
61/989,631, filed May 7, 2014, entitled, "PSYCHOTHERAPIST/PATIENT ALERT APPLICATION," incorporated herein by reference in its entirety.

BACKGROUND

Telehealth encompasses technology solutions for solving healthcare issues and, more particularly, technology solutions for providing healthcare from a distance and/or between patient in-person visits to a provider (e.g., where patient and provider are not in the same location). Email communication with physicians, teleconferences with specialists, remote consultations (via audio and/or video chat) and home monitoring of patients all fall under the telehealth umbrella. Telehealth can reduce hospitalizations and visits to an emergency room, increase quality of life, and provide healthcare services to remote locations.

Telehealth presents a number of potential challenges for patients and providers, alike. Patients may be leery of consulting with a provider over video conferencing or over the telephone that they have never met. Similarly, providers may not be comfortable diagnosing or treating a remote patient they have not met. Moreover, for specialized types of treatment, it may be more difficult for a patient to locate a suitable provider and for a provider to provide treatment without more than basic bibliographic information about a patient they have not met in person.

BRIEF SUMMARY

According to particular embodiments, systems and methods herein include an electronic therapy platform for providing improved patient and therapist matching, the electronic therapy platform including: a) one or more servers each including a database and at least one processor and operatively connected to: i) a particular patient's computing device; and ii) at least one therapist's computing device; b) a matching engine for calculating a match score of the particular patient and the at least one therapist by: i) receiving patient data items associated with patient answers to a series of patient questions presented to the particular patient at the particular patient's computing device; ii) receiving therapist data items associated with therapist answers to a series of therapist questions; iii) assigning a weight to each of the patient answers and the therapist answers; iv) determining the match score based on the weight of each of the patient answers and the therapist answers; c) an assessment engine for providing an initial assessment of the particular patient by: i) receiving assessment data items associated with patient answers to a series of assessment questions presented to the particular patient at the particular patient's computing device; ii) assigning a level of severity to each of the assessment data items; and iii) transmitting the initial assessment information to the at least one therapist's computing device; and d) a continuous care engine configured for: i) receiving schedule data items associated with the particular patient's therapy schedule; ii) associating the schedule data items with particular dates and times; iii) calculating reminder times for each of the schedule data items; and iv) transmitting at least one reminder to the particular patient based on the calculated reminder time.

In various embodiments system and methods herein include a computer-implemented method, the method including the steps of: a) transmitting an electronic therapist form to a plurality of browsers, each of the plurality of browsers associated with a particular therapist, the electronic therapist form including a plurality of therapist queries; b) receiving a modified electronic therapist form from each the plurality of browsers, each of the modified electronic therapist forms including answers to each of the plurality of therapist queries; c) assigning a weight to each answer to each of the plurality of therapist queries; d) determining, based at least in part on the assigned weight to each answer, a particular category of a number of categories to categorize each therapist; e) storing each of the modified electronic therapists forms and data regarding the category in which each therapist is categorized in memory; f) transmitting an electronic patient form to a browser associated with a particular patient, the electronic form including a plurality of patient queries; g) receiving a modified electronic form from the browser associated with the particular patient, the modified electronic patient form including an answer to each of the plurality of patient queries; h) assigning a weight to each answer to each of the plurality of patient queries; i) determining, based at least in part on the assigned weight to each answer, which of the number of categories of patients to categorize the particular patient; j) storing each of the modified electronic patient forms and information regarding which category of patient in which the particular patient is categorized in memory; k) extracting the answer to the first patient query of the plurality of patient queries; l) searching the electronic therapist forms for an answer corresponding to the answer to the first patient query and creating a preliminary set of electronic therapist forms, wherein each of the electronic therapist forms in the preliminary set include the corresponding answer; m) matching the particular patient to particular therapists corresponding to three of the preliminary set of electronic therapist forms based at least in part on the category of therapist that each of the particular therapists is categorized and the category that the particular patient is categorized; and n) displaying a profile corresponding to each of the three particular therapists on the browser associated with the particular patient.

In some embodiments, a computer-implemented method for providing remote therapy to a patient, the computer-implemented method including: a) receiving patient data items including information regarding a patient's therapy style; b) receiving therapist data items including information regarding a plurality of therapists' therapy styles; c) based upon receiving the patient data items and the therapist data items, calculating a match score for each of the plurality of therapists and the patient; d) providing the match score for each of three therapists of the plurality of therapists to the patient, wherein the three therapists include therapists with a top three-highest match scores; e) receiving an indication of a selection of one of the three therapists from the patient; f) receiving a treatment plan for the patient from a computing device associated with the selected therapist, wherein the treatment plan includes one or more events and dates and times that the one or more events take place; g) calculating a reminder time for transmitting a reminder to the patient regarding the one or more events; and h) transmitting a reminder to the patient regarding the one or more events at the reminder time.

BRIEF DESCRIPTION OF THE DRAWINGS

FIG. 1 is an exemplary system environment constructed according to one embodiment of the present disclosure.

FIG. 2 is an exemplary computer/server architecture according to one embodiment of the present disclosure.

FIGS. 3A & 3B are flow charts illustrating an exemplary matching process according to one embodiment of the present disclosure.

FIG. 4 is a flow chart illustrating an exemplary assessment process according to one embodiment of the present disclosure.

FIG. 5 is a flow chart illustrating an exemplary continuous care process according to one embodiment of the present disclosure.

FIGS. 6-8 are exemplary screenshots of a user interface including a patient matching questionnaire according to one embodiment of the present disclosure.

FIG. 9 is an exemplary screenshot of a user interface for displaying exemplary match results according to one embodiment of the present disclosure.

FIG. 10 is an exemplary screenshot of a user interface for displaying a profile of an exemplary therapist according to one embodiment of the present disclosure.

FIGS. 11-16 are exemplary screenshots of a user interface including an exemplary patient intake assessment according to one embodiment of the present disclosure.

FIG. 17 is an exemplary screenshot of a user interface for displaying an exemplary patient profile according to one embodiment of the present disclosure.

FIG. 18 is an exemplary screenshot of a user interface for displaying and managing preferred medical providers according to one embodiment of the present disclosure.

FIG. 19 is an exemplary screenshot of exemplary appointment calendar according to one embodiment of the present disclosure.

FIG. 20 is an exemplary screenshot of exemplary geolocation services according to one embodiment of the present disclosure.

DETAILED DESCRIPTION

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended, any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

According to various embodiments, systems and methods herein describe a virtual mental health/therapy platform. In particular embodiments, the systems and methods disclosed herein describe a system that includes matching a particular patient to one or more therapists, providing an initial assessment of the particular patient to the one or more therapists, and providing a continuous care application to the particular patient (e.g., to track progress and receive care plan related reminders).

In particular embodiments, the system matches the particular patient to the one or more therapists based on: 1) the particular patient's responses to patient questions designed for determining various attributes of the particular patient; and 2) the one or more therapists' responses to therapist questions designed for determining various attributes of the one or more therapists. In various embodiments, the patient questions and/or the therapist questions are delivered to the patient and therapist via the virtual therapy platform in the form of an electronic form, although it will be understood from the discussions herein that the patient and/or therapist questions may be delivered in any suitable way.

The system, in particular embodiments, assigns a weight to each of the patient and therapist answers, where the weight may be any suitable weight, such as a number, percentage, etc. According to at least one embodiment, the system assigns at least one category to the particular patient and to each of the one or more therapists based on the assigned weights. In one or more embodiments, the system calculates a match score based on the assigned categories for the particular patient and each of the one or more therapists and displays a profile of each of the top three therapists that have the highest match score for the particular patient.

In at least one embodiment, the system is configured to provide an initial assessment of a particular patient to a medical provider (therapist). In particular embodiments, the initial assessment may highlight potential issues for the particular patient, thus, potentially making it easy for the medical provider to quickly determine potential issues with the particular patient.

According to particular embodiments, the system is configured to provide a series of questions for creating the initial assessment of the particular patient. In some embodiments, the system is configured to assign a category to each answer to each of the series of questions. In at least one embodiment, based on the category of each answer to the series of questions, the system creates an initial assessment for the particular patient and transmits the initial assessment to the medical provider.

According to one or more embodiments, the system is configured to provide various functionality and features related to continuous patient care. In one embodiment, the system is configured to receive all or part of a patient's care plan, which may include therapy appointments and/or other wellness activities such as going to the gym, going to church, etc. In these embodiments (and others), the system is configured to provide reminders to the patient regarding these activities and appointments.

In some embodiments, the system is configured to batch and provide a therapist updates and/or alerts based on a patient's geolocation and/or social network activity (e.g., the system, in one or more embodiments, is configured to determine whether the patient is attending appointments, going to work, etc. based on the patient's geolocation and/or other activities) at various intervals. The system may be configured to transmit updates and/or alerts to the therapist upon determination of a potential issue with the patient daily, weekly, monthly, etc.

Exemplary Technical Platforms

As will be appreciated by one skilled in the relevant field, the present systems and methods may be, for example, embodied as a computer system, a method, or a computer program product. Accordingly, various embodiments may take the form of an entirely hardware embodiment, an entirely software embodiment, or an embodiment combining software and hardware aspects. Furthermore, particular embodiments may take the form of a computer program product stored on a computer-readable storage medium having computer-readable instructions (e.g., software) embodied in the storage medium. Various embodiments may take the form of web-implemented computer software. Any suitable computer-readable storage medium may be utilized including, for example, hard disks, compact disks, DVDs, optical storage devices, thumb drives, solid state drives, and/or magnetic storage devices.

Various embodiments are described below with reference to block diagrams and flowchart illustrations of methods, apparatuses (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a special purpose computer or other programmable data processing apparatus to produce a machine, such that the instructions that execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of mechanisms for performing the specified functions, combinations of steps for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and other hardware executing appropriate computer instructions.

Exemplary System Architecture

As discussed above, various systems and methods herein describe a platform for matching medical providers, including therapists, to patients as well as for providing a platform for medical providers and patients to interact and communicate. As will be understood by one of ordinary skill in the art, these systems and methods may be implemented in any suitable way. The following is a description of exemplary architecture and is but one example of how the herein described systems and methods may be implemented.

FIG. 1 is a block diagram of a system 100 according to a particular embodiment. As may be understood from this figure, the system 100 includes one or more computer networks 115, a virtual therapy platform 200, a database 140, a patient mobile computing device 150 (e.g., such as a smart phone, a tablet computer, a wearable computing device, a laptop computer, etc.), a patient desktop computing device 160, a medical provider mobile computing device 170 (e.g., such as a smart phone, a tablet computer, a wearable computing device (e.g., health monitors, connected watches, connected glasses, fitness wearables, a laptop computer, etc.), and a medical provider desktop computing device 180. In particular embodiments, the one or more computer networks 115 facilitate communication between the virtual therapy platform 200, database 140, and one or more computing devices 150, 160, 170, and 180.

The one or more computer networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computers). The communication link between the virtual therapy platform 200 and the database 140 may be, for example, implemented via a Local Area Network (LAN) or via the Internet.

Figure 6:
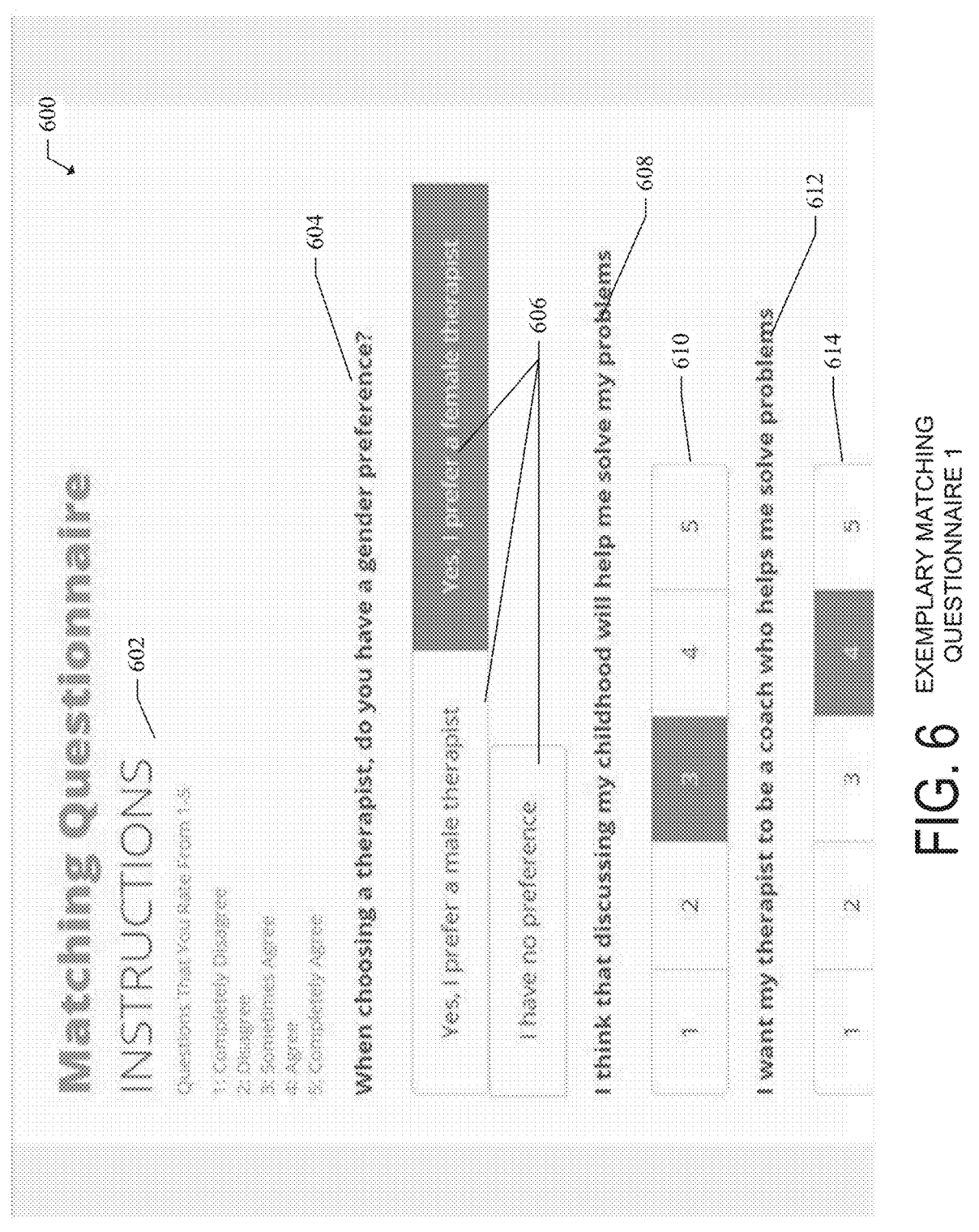

In the exemplary embodiment shown in FIG. 1, the virtual therapy engine 200 includes a matching engine 300, an assessment engine 400, and a continuous care engine 500. The matching engine 300, in one or more embodiments, receives data from patients and medical providers and ranks potential medical provider matches to each patient. This process is further discussed below, particularly in relation to FIGS. 3A and 3B. The assessment engine 400, in at least one embodiment, receives data from patients and provides an initial assessment of the patient to a medical provider. As will be further discussed herein, the functionality of the assessment engine 400 may be utilized before or after the matching engine 300 matches the patient and the medical provider. The continuous care engine 500, in particular embodiments, provides reminders and calendar notifications based a therapy plan, which may be uploaded to the system by a patient and/or a therapist, tracks patient activities, batches these activities and transmits these activities to the therapist, and provides alerts to patient contacts (including the therapist) in certain situations. The continuous care engine 500 will be further discussed below in relation to FIG. 6.

In particular embodiments, the patient mobile device 150 and the medical provider mobile computing device 170 are configured to download a mobile application 156 or 176, respectively (collectively "mobile application 156/176"). As will be understood by one of ordinary skill in the art, the mobile application 156/176 may represent any suitable instance or portion of the systems and methods described herein that is stored locally on any of the one or more computing devices 150 and/or 170.

As a particular example, a user, such as a patient or medical provider, downloads an application (or "App") from an application store (e.g., mobile application 156/176), which is stored on the user's mobile device (e.g., the patient mobile computing device 150 or medical provider mobile computing device 170). Continuing with this particular example, the mobile application 156/176 includes various components of the systems and methods described herein, such as a log in and interface for interacting with the virtual therapy platform 200. The mobile application 156/176, in this particular example, communicates (e.g., via the one or more networks 115) with the virtual therapy platform 200 to receive/retrieve and/or transmit content or data (e.g., shareable media, statistics, user account/profile information, etc.) for use in the mobile application 156/176 on the user's mobile device. In various embodiments, the mobile application 156/176 interacts with one or more social networks via a suitable API. In further embodiments, the mobile application 156/176 accesses a mobile device's geolocation services for use with locating and recording locations of a patient.

FIG. 2 illustrates a diagrammatic representation, in various embodiments, of the architecture of an exemplary computer that can be used within the system 100, for example, as a client computer (e.g., one of the one or more computing devices 150, 160, 170, 180, as shown in FIG. 1) or as a server computer (e.g., part of one or more virtual therapy platform servers 200, shown in FIG. 1). In particular embodiments, the architecture of the virtual therapy platform 200 may be suitable for use as a computer within the context of the system 100 that is configured to enable patient and medical provider matching, providing an initial assessment of a patient, and providing continuous care functionality, among other various functions. For purposes of clarity and brevity, the exemplary computer shown in FIG. 2 will be referred to as the virtual therapy platform 200, although it should be understood that this exemplary computer may represent any suitable computing device associated with the systems and methods described herein.

In particular embodiments, the virtual therapy platform 200 may be connected (e.g., networked) to other computers in a LAN, an intranet, an extranet, and/or the Internet. As noted above, the virtual therapy platform 200 may operate in the capacity of a server, a client computer in a client-server network environment, and/or as a peer computer in a peer-to-peer (or distributed) network environment. The virtual therapy platform 200 may be a desktop personal computer (PC), a tablet PC, a set-top box (STB), a Personal Digital Assistant (PDA), a cellular telephone, a smartphone, a tablet, a wearable computing device, a web appliance, a server, a network router, a switch or bridge, or any other computer capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein.

An exemplary virtual therapy platform 200 includes a processor 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processor 202 represents one or more processors such as a microprocessor, a central processing unit, or the like. More particularly, the processor 202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. The processor 202 may also be one or more special-purpose processors such as an application specific integrated circuit (ASIC), a field programmable gate array (FPGA), a digital signal processor (DSP), a network processor, or the like. The processor 202 may be configured to execute processing logic 226 for performing various operations and steps discussed herein.

The virtual therapy platform 200 may further include a network interface device 208. The virtual therapy platform 200 also may include a video display unit 210 (e.g., a liquid crystal display (LCD) or a cathode ray tube (CRT)), an alphanumeric input device 212 (e.g., a keyboard), a cursor control device 214 (e.g., a mouse), and a signal generation device 216 (e.g., a speaker).

While the machine-accessible storage medium 230 is shown in an exemplary embodiment to be a single medium, the term "computer-accessible storage medium" should be understood to include a single medium or multiple media (e.g., a centralized or distributed database, and/or associated caches and servers) that store the one or more sets of instructions. The term "computer-accessible storage medium" should also be understood to include any medium that is capable of storing, encoding or carrying a set of instructions for execution by the computer and that cause the computer to perform any one or more of the methodologies of the present systems and methods. The term "computer-accessible storage medium" should accordingly be understood to include, but not be limited to, solid-state memories, optical and magnetic media, etc.

The data storage device 218 may include a machine-accessible storage medium 230 (also known as a non-transitory computer-readable storage medium or a non-transitory computer-readable medium) on which is stored one or more sets of instructions (e.g., software 222) embodying any one or more of the methodologies or functions described herein. The software 222 may also reside, completely or at least partially, within the main memory 204 and/or within the processor 202 during execution thereof by the virtual therapy platform 200—the main memory 204 and the processor 202 also constituting computer-accessible storage media. The software 222 may further be transmitted or received over a network 115 via a network interface device 208.

The software 222 may represent any number of program modules, including, but not limited to an operating system (not shown), the matching engine 300, the assessment engine 400, and/or the continuous care engine 500. For simplicity and brevity, these engines are merely exemplary and may represent a number of program modules that control certain aspects of the operation of the virtual therapy platform 200. The matching engine 300, the assessment engine 400, and the continuous care engine 500 are described in more detail below.

Exemplar System Functionality

As will be understood from discussions herein, the virtual therapy platform 200, in various embodiments, is a platform for matching a particular patient to a particular medical provider (such as a therapist), providing an initial assessment of the particular patient to the particular medical provider, and providing a platform for the particular patient and particular medical provider to interact, hold virtual (telehealth) treatment sessions, and track continuous care of the particular patient. Particular embodiments and functionality of the virtual therapy platform 200 are discussed below.

Exemplary Patient/Therapist Matching

FIGS. 3A and 3B depict various exemplary process steps of the matching engine 300. As discussed above, in various embodiments, when a particular patient logs into the virtual therapy platform 200 for the first time, they may be asked a series of questions designed to assess their "therapy style," which may include the particular patient's outlook on life, personal approach to solving problems, and/or a framework for providing therapy. In particular embodiments, the particular patient is then presented with a top three therapists that may be a good match for the particular patient, at least partially based on the patient's therapy style. Although the present embodiments are discussed in the context of a "therapist," it will be understood that the present systems and methods may be used for any suitable medical provider, including, but not limited to, doctors, dentists, medical specialists, psychotherapists, counselors, psychologists, etc.

Turning now to FIG. 3A, the exemplary process 300 begins at step 310, where the system is configured to transmit (e.g., facilitate display of) an electronic therapist form to a therapist, the electronic therapist form including one or more therapist questions. In various embodiments, the electronic therapist form may be transmitted to the therapist from the virtual therapy platform and displayed in any suitable way, such as via a browser (e.g., on the medical provider desktop computing device 180) or via a mobile application (e.g., on the medical provider mobile computing device 170).

The electronic therapist form may be in any suitable electronic representation of the one or more therapist questions. In embodiments further discussed herein, the electronic therapist form is a single electronic form displayed on a web browser, where a user can select answers (e.g., multiple choice answers, true or false answers, etc.) to the questions and then submit the entire form at once. In some embodiments, the electronic therapist form is a series of questions that are transmitted and/or displayed to the user (e.g., an answer to a first question prompts the transmission or display of the second questions and an answer to the second question prompts the transmission or display of the third question, and so on). In further embodiments, the one or more therapist questions are transmitted to the therapist by email, text message, social network message, etc.

The one or more therapist questions may be any suitable questions for matching the therapist to a particular patient (the one or more therapist questions may also be known as one or more therapist queries). In at least one embodiment, the one or more therapist questions are directed to determining the therapist's therapy style (e.g., optimal therapy style, outlook on life, personal approach to solving problems, etc.), which will be understood by one of ordinary skill in the art to include, for example, emperiricism (cognitive-behavioral), rationalism (psychodynamic), humanism (humanistic), and collectivism (systemic). In particular embodiments, the one or more therapist questions may be general questions about the therapist, such as, for example, location of the therapist, sex of the therapist, race of the therapist, age of the therapist, cost structure of the therapist's practice, etc.

At step 315, the system is configured to receive answers to the one or more therapist questions. In various embodiments, the answers to the one or more therapist questions are in the form of a multiple choice selection (e.g., a selection of an answer corresponding to a, b, c, or 1, 2, 3, 4, 5, or x, y, z, etc.). In some embodiments, the answers to the one or therapist questions are in the form of short answer or a brief typed/written answer to each of the one or more therapist questions. In at least one embodiment, the answers to the one or more therapist questions are in the form of "true/false." In further embodiments, the answers to the one or more therapist questions are in the form of responses to text messages, email messages, or other electronic messaging technologies.

At step 320, the system is configured to assign a weight to each of the therapist answers. In various embodiments, the system is configured to assign the weight for each answer, separately. In some embodiments, the system is configured to assign the weight to each of the answers in aggregate (e.g., all the answers get the same weight or an average weight). As will be understood by one of ordinary skill in the art, the weight assigned to each answer may be any suitable weight (e.g., a whole number, a fraction, a percentage) and may be applied to each answer in any suitable way.

At step 325, the system is configured to determine at least one category for the therapist based on the weight assigned to each of the answers. In particular embodiments, each category corresponds to a particular weight or combination of weights assigned to each answer. Each category may be any suitable category, such as, but not limited to therapy styles (emperiricism (cognitive-behavioral), rationalism (psychodynamic), humanism (humanistic), and collectivism (systemic)), personality types, likes, dislikes, etc.

At step 330, the system is configured to store answers to the one or more therapist questions, the weights assigned to each of the answers, and the category determined for the therapist in memory. In particular embodiments, the system is configured to store the above information in the database 140 (as shown in FIG. 1).

At step 335, the system is configured to transmit an electronic form to a patient, the electronic patient form including one or more patient questions. In particular embodiments, the patient electronic form is in the same form as the therapist electronic form as discussed above at step 310. In some embodiments, the patient electronic form is in a different form than that therapist electronic form discussed at step 310 (e.g., the therapist electronic form is a single electronic form and the patient electronic form is a series of questions, etc.).

The one or more patient questions may be any suitable questions for matching the patient to one or more therapists (the one or more patient questions may also be known as one or more patient queries). In at least one embodiment, the one or more patient questions are directed to determining the patient's optimal therapy style, which will be understood by one of ordinary skill in the art to include, for example, emperiricism (cognitive-behavioral), rationalism (psychodynamic), humanism (humanistic), and collectivism (systemic). In particular embodiments, the one or more patient questions may be general questions about the therapist, such as, for example, location of the therapist, sex of the therapist, race of the therapist, age of the therapist, cost structure of the therapist's practice, etc. As will be understood by one of ordinary skill in the art, the therapist questions and patient questions may be the same or different questions (or a different number of questions).

At step 340, the system is configured to receive an answer to each of the plurality of patient questions. The system, in some embodiments, is configured to receive the answers to each of the plurality of patient questions in any of the ways the system is configured to receive the therapist answers as discussed in relation to step 315.

Continuing with this exemplary process in FIG. 3B, at step 350, the system is configured to assign a weight to each patient answer. In various embodiments, the system is configured to assign the weight for each answer, separately. In some embodiments, the system is configured to assign the weight to each of the answers in aggregate (e.g., all the answers get the same weight or an average weight). As will be understood by one of ordinary skill in the art, the weight assigned to each answer may be any suitable weight (e.g., a whole number, a fraction, a percentage) and may be applied to each answer in any suitable way.

At step 355, the system is configured to determine a category for the patient based on the weight assigned to each of the answers. In particular embodiments, each category corresponds to a particular weight or combination of weights assigned to each answer. Each category may be any suitable category, such as, but not limited to therapy styles (emperiricism (cognitive-behavioral), rationalism (psychodynamic), humanism (humanistic), and collectivism (systemic)), personality types, likes, dislikes, etc. As will be understood by one of ordinary skill in the art, the categories for the patient may or may not be the same categories for the therapist (e.g., therapist may be assigned categories by therapy styles and patients may be assigned categories based on personality types).

At step 360, the system is configured to store answers to the one or more patient questions, the weights assigned to each of the answers, and the category determined for the patient in memory. In particular embodiments, the system is configured to store the above information in the database 140 (as shown in FIG. 1).

At step 365, the system is configured to extract the answer to the first patient question from memory. In various embodiments, answer to the first patient question may be a threshold question such as basic preferences for a therapist, including, but not limited to, a therapist in a particular age range, a therapist of a particular sex, etc. As will be understood by one of ordinary skill in the art, the system, in at least one embodiment, may include more than one threshold question.

At step 370, the system is configured to search (e.g., locate) the stored therapist answers for answers corresponding to the first patient answer. In various embodiments, the system is configured to search the stored therapists answers for the answer corresponding to the first patient answer by examining a particular corresponding question in each of the stored electronic therapist forms. In some embodiments, the system is configured to pre-sort each therapist based in part on the first patient answer (e.g., the system is configured to group therapists by sex, age, and/or race in anticipation of threshold first patient answers).

At step 375, the system is configured to create a preliminary set of therapists that includes therapists with answers that correspond to the first patient answer. In various embodiments, the system is configured to create the set of therapists that correspond to the first patient answer each time a new patient answers the first question. In some embodiments, the system is configured to create the set of therapists that correspond to the first patient answer by adding each new therapist to a predefined set (e.g., a set of male therapists, a set of female therapists, etc.).

At step 380, the system is configured to determine a match score for each of the therapists in the preliminary set of therapists based on the category of each of the therapists and the category of the patient. According to a particular embodiment, the system is configured to determine the match score for each of the therapists in the preliminary set of therapists based on the category of each therapist and the category of each patient by determining a percent match of the patient and each therapist within the preliminary set of therapists. In various embodiments, the system is configured to determine the match score for each of the therapists in the preliminary set of therapists based on the category of each therapist and the category of each patient by ranking each therapist in the preliminary set and assigning each therapist a score based on this ranking.

At step 385, the system is configured to display a profile corresponding to each of the therapists with the top three match scores. In particular embodiments, the system is configured to display a list of the top three therapist matches for the patient based on the match score. As will be understood by one of ordinary skill in the art, the system may be configured to display any particular number of matched therapists (e.g., one, two, five, ten, twenty, etc.).

Exemplary Assessment Process

As discussed herein, the present systems and methods may provide an initial assessment of a particular patient to a therapist (e.g., upon a match of the particular patient to the therapist, as described above). According to particular embodiments, the initial assessment may indicate to the therapist one or more potential issues of the particular patient. The system may utilize any suitable method for providing the initial assessment of the particular patient to the therapist. Such an exemplary process is shown in FIG. 4 and discussed below.

Beginning with step 410, the system is configured to receive assessment data items associated with patient answers to a series of assessment questions presented to the particular patient at the particular patient's computing device. In various embodiments, the system is configured to transmit the series of assessment questions to the particular patient's computing device via an electronic form (e.g., to the particular patient's web browser or application associated with the present systems and methods). In some embodiments, the system is configured to transmit the series of assessment questions to the particular patient's computing device via email, text message, social network message, or any other suitable messaging or electronic transmission technology.

The series of questions may be any suitable questions to provide an initial assessment of the particular patient. In various embodiments, the series of questions may include questions regarding the mental health and/or previous diagnosis of the particular patient. In particular embodiments, the series of questions may or may not include questions regarding the medical history of the particular patient. In some embodiments, the series of questions include questions designed to indirectly ascertain mental health issues of the particular patient.

In particular embodiments, in response to receiving the series of assessment questions, the particular patient responds to/answers each question in the series of assessment questions and transmits these responses/answers to the system. In various embodiments, the answers to the series of questions are in the form of a multiple choice selection (e.g., a selection of an answer corresponding to a, b, c, or 1, 2, 3, 4, 5, or x, y, z, etc.). In some embodiments, the answers to the series of questions are in the form of short answer or a brief typed/written answer to each of the one or more therapist questions. In at least one embodiment, the answers to the series of questions are in the form of "true/false."

At step 420, the system is configured to assign a level of severity to each of the assessment data items based on the patient answers. In various embodiments, the system is configured to assign severity levels ranging from "high" to "low." In some embodiments, the system is configured to assign severity levels on a numerical scale (e.g., 1-10, 1-50, 1-100, etc.). In one or more embodiments, the system is configured to assign severity levels based on a graded color spectrum, wherein red is the most severe and green is the least severe. As a particular example, if the particular patient provides an answer to a particular question of the series of assessment questions that indicates that the particular patient is severely depressed, the system may assign the data item associated with the patient answer a severity level of "high." As will be understood by one of ordinary skill in the art, the system may be configured to assign the level of severity to each of the assessment data items or may assign the level of severity based on a combination of data items (e.g., the particular patient has answered a number of questions that indicate that the particular patient is depressed and, thus, a severity level of "high" may be assigned to each of the data items associated with questions associated with depression). Other non-limiting examples of potential patient issues include post-traumatic stress syndrome (PTSD), anxiety, etc.

At step 430, the system is configured to transmit the initial assessment information to the at least one therapist's computing device. In various embodiments, the system is configured to transmit the initial assessment information to the at least one therapist's computing device via an email, a text message, a message via the at least one therapist's browser, a message on an application associated with the system as discussed herein, etc.

Exemplary Continuous Care Process

As discussed herein, the virtual therapy platform, in various embodiments provides continuous care functionality, including transmitting reminders of therapy tasks to patients. An exemplary process of transmitting reminders regarding therapy-related tasks is discussed below in related to FIG. 5.

At step 510, the system is configured to receive schedule data items associated with the particular patient's therapy schedule. In various embodiments, the system is configured to receive the schedule data items associated with the particular patient's therapy schedule from a computing device associated with the particular patient. In some embodiments, the system is configured to receive the schedule data items associated with the particular patient's therapy schedule from a therapist.

The schedule data items may be any suitable schedule data items. In various embodiments, the schedule data items are items associated with tasks specific to the particular patient's therapy. Non-limiting examples of suitable schedule data items include taking medication, exercising, diet reminders, engaging in meditation, attending church, listening to calming music, listening to positive affirmations, writing in a journal (journaling in general), etc.

At step 520, the system is configured to associate the schedule data items with particular dates and times. In various embodiments, the system is configured to receive a particular date and/or time with each schedule data item (e.g., a schedule of tasks). In some embodiments, the system is configured to receive particular dates and/or times for multiple schedule data items. In further embodiments, the system is configured to receive a calendar of schedule data items (e.g., via a calendar import or the like).

At step 530, the system is configured to calculate reminder times for each of the schedule data items. In various embodiments, the system receives particular times for reminders for each schedule data item (e.g., the particular times for the reminders may be a reminder 10 minutes before the time of an event, a reminder at the time of the event, etc.). In these embodiments (and others), the system is configured to calculate a time corresponding to the received particular time to send the reminder (e.g., if the particular time for the reminder is 10 minutes and the event is at 3:30 PM, the system may calculate that the time to send a reminder is at 3:20 PM). As will be understood, in some embodiments, the particular patient or the particular patient's therapist may set standard reminder times (e.g., 10 minutes prior to an event, at the time of the event, etc.).

At step 540, the system is configured to transmit at least one reminder to the particular patient based on the calculated reminder time. As discussed herein, the system may be configured to transmit the at least one reminder to the particular patient in any suitable way, including via text message, instant message, email, an application on a mobile device, browser-based reminder, etc.

Exemplary User Interface

FIGS. 6-19 provide examples of the systems and methods described herein within the context of a website or application. Particularly, FIGS. 6-10 depict exemplary screenshots of various user interfaces for matching a particular patient to a particular therapist. FIGS. 11-16 depict exemplary screenshots of various user interfaces for completing an intake assessment for a particular patient, and FIGS. 17-19 depict various user interfaces for various other features and functionality of the systems and methods disclosed herein. As will be understood from the discussions herein, any questions or answers shown in the FIGS. are intended to exemplary only.

FIGS. 6-8 depict exemplary screenshots of a user interface including a patient matching questionnaire according to one embodiment of the present disclosure. In the embodiment shown in FIG. 6, the exemplary patient matching questionnaire includes instructions for filling out the form, 602. The exemplary matching questionnaire, in particular embodiments, includes a first question 604 ("do you have a gender preference") and electronic buttons for the patient to respond to the question. In various embodiments, the exemplary matching questionnaire includes more questions 608 and 612 and buttons 610 and 614 for answering questions 608 and 612. As will be understand by discussions herein, the system may be configured to enable the patient to answer questions in any suitable way, including by a button (e.g., by clicking or otherwise selecting a button), a text box, a radio button, making a selection, tapping a location on a screen, etc.

FIGS. 7 and 8 depict more questions of the patient matching questionnaire 600, including questions 616, 620, 624, 628, 632, 636, 640, 644, and 648 and respective answer buttons 618, 622, 626, 630, 634, 638, 642, 646, and 650. In particular embodiments, patient matching questionnaire 600 further includes a button for submitting the patient answers 652. As will be understood from discussions herein, the submission button 652, upon activation, submits the patient's answers to the questions as indicated in the various answer buttons on the electronic form.

FIG. 9 is an exemplary screenshot of a user interface for displaying exemplary match results according to one embodiment of the present disclosure. As will be understood from discussions herein, the exemplary match results are displayed to the user/patient upon completion and/or submission of the patient matching questionnaire 600 (above). In various embodiments, upon submission of the patient matching questionnaire, the system is configured to calculate match scores of a plurality of therapists for the particular patient. As shown in the embodiment shown in FIG. 9, the system is configured to display the top three results based on match score.

As shown in FIG. 9, the exemplary match results user interface includes a title of the page 902, information regarding a first matched therapist 920, information regarding a second matched therapist 940, and information regarding a third matched therapist 960. For simplicity and brevity, the information regarding the first matched therapist 920 will be used as an example.

According to particular embodiments, the information regarding the first matched therapist 920 includes a profile picture of the first matched therapist 922, a name of the first matched therapist 924, and may include other relevant information (not numbered). In various embodiments, the information regarding the first matched therapist 920 includes a match score of the first matched therapist with the particular patient 926, a button that allows the particular patient to connect the first matched therapist (e.g., by electronic message, by secure teleconference, by phone, etc.) 928, a button for accessing the first matched therapist's full profile 930, and other options, such as options for saving the first matched therapist or removing the first matched therapist from a saved group of therapists 932.

FIG. 10 is an exemplary screenshot of a user interface for displaying a profile of an exemplary therapist 1000 according to one embodiment of the present disclosure (e.g., which may be accessed, for example, upon a patient selecting button 930 in FIG. 9). In the embodiment shown in FIG. 10, the exemplary profile of the exemplary therapist 1000 includes a therapist name 1002, a therapist profile picture 1004, personal and contact information for the therapist 1006 (e.g., email address, phone number, etc.), a price of the therapist (e.g., how much the therapist charges per hour, per telehealth session, etc.), and a video 1010 (e.g., an introductory video featuring the therapist and/or the therapist's practice).

The various systems and methods herein may be configured to provide an initial assessment of a particular patient. In particular embodiments, the system provides the initial assessment of the particular patient based on the particular patient's answers to a series of questions. Exemplary initial assessment questions are shown at FIGS. 11-16.

FIG. 11 depicts a user interface including an exemplary patient intake assessment form 1100 according to one embodiment of the present disclosure. In the embodiment shown in FIG. 11, the exemplary patient intake assessment form including instructions for filling out the form, 1102. The exemplary patient intake form 1100, in the embodiment shown in FIG. 11, further includes a series of questions for a patient, 1104 and 1108 and electronic buttons 1106 and 1110 for answering the series of questions. As will be understood from discussions herein, the electronic buttons 1106 and 1110 may be any suitable mechanism discussed herein for recording the patient's answers to the series of questions.

FIGS. 12-16 depict further exemplary questions of the series of questions of the exemplary patient intake form 1100, including questions 1112, 1116, 1120, 1124, 1128, 1132, 1136, 1140, 1144, 1146, 1148, 1152, 1156, 1160, 1164, 1168, 1172, and 1176 and respective answer buttons 1114, 1118, 1122, 1126, 1130, 1134, 1138, 1142, 1145, 1147, 1150, 1154, 1158, 1162, 1166, 1170, 1174, and 1178. In particular embodiments, the exemplary patient intake assessment form 1100 further includes a button for submitting the patient answers 1180. As will be understood from discussions herein, the submission button 1180, upon activation, submits the patient's answers to the questions as indicated in the various answer buttons on the electronic form.

FIG. 17 depicts an exemplary screenshot of a user interface for displaying an exemplary patient profile 1700 according to one embodiment of the present disclosure. The exemplary patient profile 1700 includes, in the embodiment shown, a view of the patient profile 1702 and various navigation options 1703. The view of the patient profile 1702 includes, in the embodiment shown, a profile picture for the patient and basic information about the patient, such as a brief description of the patient and geolocation indicating where the patient is located. The various navigation options 1703 include a profile editing navigation button, a button for accessing the patient's account, a button for viewing saved therapists, and a button for enabling the patient to log out of the system. The exemplary patient profile 1700 further includes various navigation buttons 1705, which may include a home button, a message button (e.g., for sending and receiving secure/encrypted and HIPAA compliant messages, including video messaging), an appointments button, and an account button. As will be understood from discussions herein, the various navigation options 1703 and 1705 may include any other suitable navigation options.

The exemplary patient profile 1700 includes, in the embodiment shown, an indication of the type of profile and/or other basic information 1710 (e.g., "public profile" vs. "private profile", where a public profile may be generally findable by other users of the system and a private profile may not be findable). In various embodiments, the system may be configured to enable the patient to edit their profile, including editing their profile picture at 1714 and 1716, previewing and saving profile changes at 1712, and adding basic biographical information at 1718. As will be understood from discussions herein, therapists (or other medical providers) may have substantially similar profiles and options as shown for an exemplary patient.

FIG. 18 is an exemplary screenshot of a user interface for displaying and managing preferred medical providers 1800 according to one embodiment of the present disclosure. As shown in the embodiment of FIG. 18, the user interface for displaying and managing preferred medical providers 1800 includes the patient's profile 1702 and navigation options 1703 and 1705, as discussed in relation to FIG. 17. In various embodiments, the user interface for displaying and managing preferred medical providers 1800 includes preferred or saved therapists for the patient. In these embodiments, as shown in FIG. 18, the user interface for displaying and managing preferred medical providers 1800 includes a photograph or avatar for each preferred or saved therapist 1802 and an indication of whether each preferred/saved therapist is currently online. As will be understood from discussion herein, if a particular preferred/saved therapist is listed as "online" (or the like), the system may be configured to enable the patient to immediately interact with the online therapist via messaging or videoconferencing.

FIG. 19 is an exemplary screenshot of exemplary appointment calendar 1900 according to one embodiment of the present disclosure. As shown in the embodiment of FIG. 19, the exemplary appointment calendar 1900 includes the patient's profile 1702 and navigation options 1703 and 1705, as discussed in relation to FIG. 17. In various embodiments, the exemplary appointment calendar 1900 includes various appointments for a patient (or therapist). In particular embodiments, each appointment includes a status of the appointment 1902 (e.g., completed, upcoming, open, etc.), a patient/therapist name 1904 (e.g., name of the patient or therapist associated with the appointment), a start time 1906, an end time 1908, and options 1910 (e.g., options for alerts, for reminders, etc.).

FIG. 20 is an exemplary screenshot of exemplary geolocation services according to one embodiment of the present disclosure. As shown in FIG. 20, systems and methods herein may utilize a mobile device's geolocation services to track a location of a patient for any of the purposes discussed herein.

Additional Features

Patient Tracking

In various embodiments, the systems and methods herein may include patient tracking. In a particular embodiment, the system is configured (via an App) to access a patient's mobile device geolocation capabilities (e.g., via one or more suitable APIs) to determine a location of the patient at any suitable time. The system may, for example, determine whether the patient has completed tasks in the patient's continuous care plan. Continuing with this example, a therapist may receive one or more alerts (via the system) when a patient does not complete a particular task in the patient's continuous care plan.

A particular example may be useful. In this particular example, a particular patient has downloaded a continuous care application (of the systems and methods herein) to their mobile computing device. Continuing with this particular example, the particular patient and/or the particular patient's therapist has uploaded or input tasks of a continuous care plan to the system (as discussed above). In this particular example, the particular patient's continuous care plan includes going to the gym on Wednesday, going to a yoga class on Thursday, and going to church on Friday.

Continuing with this particular example, the particular patient does not attend the gym on Wednesday. The system, in this particular example, by accessing/receiving geolocations from the particular patient's mobile device, determines that the particular patient was not as the gym on Wednesday (e.g., the system has a stored location or approximate location of the gym and can compare this location to locations visited by the particular patient on Wednesday to determine whether the particular patient went to the gym). Using a substantially similar process, the system, in this particular example, determines the particular patient did not go to yoga on Thursday or church on Friday. The system, in some embodiments, may produce one or more alerts to be transmitted to the therapist upon determining that the particular patient is not adhering to the continuous care plan.

The system, continuing with this particular example, may be configured to batch the geolocations of the particular patient and/or alerts regarding the particular patient's failure to adhere to the continuous care plan and may transmit the geolocations and/or alerts to the therapist (and/or emergency contacts of the particular patient) in any suitable frequency, such as daily, weekly, during a particular time period (e.g., the first two weeks of therapy, the first month of therapy, etc.). In further embodiments, the system may be configured to send an alert to the therapist and/or the particular patient's emergency contacts (via phone, text, email, social network message, etc.) upon determining via geolocation that the particular patient has not left their house for a particular number of days (potentially indicating an emergency).

Social Media Interaction

In various embodiments, the system may transmit data to and receive data from a patient's social networks. In these embodiments (and others), the system is configured to communication with the patient's social networks (e.g., Facebook, twitter, LinkedIN, Yik Yak, etc.) via a suitable API, by the patient providing their login credentials to the social media networks.

The system may be configured to receive the patient's activity on the social media networks and produce alerts to emergency contacts and/or the patient's therapist based on the patient's interaction with the social network. As a particular example, the system may be configured to alert the patient's therapist if the patient posts various key words or phrases on the social network potentially indicating that the patient is having a crisis, breakdown, or other event relevant to the patient's care (e.g., "having a dark day", "life sucks", etc.). Further, the system may be configured to determine whether the patient has reached a particular life event based on information received from the social network(s), such as, but not limited to, the patient's birthday, if the patient is involved with a separation from a signification other, if the patient enters a relationship, etc.

Emergency Alerts

As discussed herein, the system may be configured to notify a patient's therapist and/or emergency contacts in the case of an emergency. In particular embodiments, the systems and methods herein may include a one-touch emergency notification feature. In these embodiments, the system may be configured to alert the patient's family members, therapist, and/or an emergency help line (e.g., a national suicide prevention hotline), upon the push of a single button. The system may be configured to call, text, instant message, and/or email the patient's emergency contacts simultaneously upon activation of the one-touch emergency notification feature.

CONCLUSION

The foregoing description of the exemplary embodiments has been presented only for the purposes of illustration and description and is not intended to be exhaustive or to limit the present systems and methods to the precise forms disclosed. Many modifications and variations are possible in light of the above teaching.

The embodiments were chosen and described in order to explain the principles of the present systems and methods and their practical application so as to enable others skilled in the art to utilize the present systems and methods and various embodiments and with various modifications as are suited to the particular use contemplated. Alternative embodiments will become apparent to those skilled in the art to which the present systems and methods pertain without departing from their spirit and scope.

What is claimed is:

1. A computer-implemented method, the method comprising the steps of:
    facilitating display of an electronic therapist form on a plurality of browsers, each of the plurality of browsers associated with a particular therapist, the electronic therapist form comprising a plurality of therapist queries;
    receiving a modified electronic therapist form from each of the plurality of browsers, each of the modified electronic therapist forms comprising answers to each of the plurality of therapist queries;
    assigning a weight to each answer to each of the plurality of therapist queries;
    determining, based at least in part on the assigned weight to each answer, a particular category of a number of categories to categorize each therapist, wherein the number of categories include at least one therapy style selected from a group comprising empiricism, rationalism, humanism, and collectivism;
    storing each of the modified electronic therapists forms and data regarding the category in which each therapist is categorized in memory;
    facilitating display of an electronic patient form on a browser associated with a particular patient, the electronic patient form comprising a plurality of patient queries;
    receiving a modified patient electronic form from the browser associated with the particular patient, the modified electronic patient form comprising an answer to each of the plurality of patient queries;
    assigning a weight to each answer to each of the plurality of patient queries;

determining, based at least in part on the assigned weight to each answer, which of the number of categories of patients to categorize the particular patient;

storing each of the modified electronic patient forms and information regarding which category of patient in which the particular patient is categorized in memory;

extracting the answer to a first patient query of the plurality of patient queries from a modified electronic patient form associated with the particular patient stored in memory;

searching the electronic therapist forms for an answer corresponding to the answer to the first patient query and creating a preliminary set of electronic therapist forms in memory, wherein each of the electronic therapist forms in the preliminary set comprise the corresponding answer;

determining a match score for each of the electronic therapist forms in the preliminary set of electronic therapist forms by determining a percent match of the particular patient and each of the electronic therapist forms;

matching, via a matching engine, the particular patient to particular therapists corresponding to three of the preliminary set of electronic therapist forms based at least in part on the category of therapist that each of the particular therapists is categorized, the match score for each electronic therapist form in the preliminary set of electronic therapist forms, and the category that the particular patient is categorized;

modifying the display of the browser associated with the particular patient such that the browser displays a profile corresponding to each of the three particular therapists associated with the particular patient;

receiving a selection of a selected therapist of the three particular therapists;

receiving a care plan comprising a plurality of tasks for the particular patient;

accessing, via at least one API, geolocation data comprising a plurality of geolocations of the particular patient by accessing a mobile device of the particular patient to record locations of the particular patient; and determining that the particular patient failed to perform at least one task of the plurality of tasks based on the geolocation data.

2. The computer-implemented method claim 1, wherein the number of categories correspond to major systems of psychotherapy.

3. The computer-implemented method claim 1, wherein the particular patient may be categorized in more than one of the number of categories.

4. The computer-implemented method of claim 1, the method further comprising the step of:

receiving a selection of one of the three particular therapists from the browser associated with the particular patient;

based at least in part on receiving the selection, transmitting, to the browser associated with the particular patient, an initial assessment form, the initial assessment form comprising one or more assessment questions;

receiving an assessment answer for each of the one or more assessment questions from the browser associated with the particular patient;

assigning a weight to each assessment answer;

determining a level of severity for each assessment answer based on the assigned weight; and transmitting data associated with the level of severity for each assessment answer to a browser associated with the selected one of the three particular therapists.

5. The computer-implemented method of claim 4, wherein the method further comprises enabling the particular patient to conduct a remote therapy session with the selected one of the three particular therapists.

6. The computer-implemented method of claim 1, when the method further comprises providing an indication of whether each of the three particular therapists is currently online.

7. The computer-implemented method of claim 1, further comprising, in response to determining that the particular patient failed to perform the at least one task based on the geolocation data, generating at least one alert to the selected therapist.

8. The computer-implemented method of claim 1, further comprising in response to determining that the particular patient failed to perform the at least one task based on the geolocation data, transmitting a current geolocation to the selected therapist.

9. The computer-implemented method of claim 8, wherein the current geolocation is transmitted at a predetermined frequency.

10. The computer-implemented method of claim 1, further comprising batching the geolocation data.

11. The computer-implemented method of claim 1, wherein the care plan is received from the selected therapist.

12. The computer-implemented method of claim 1, further comprising generating a patient profile interface comprising descriptive information and a geolocation indicating where the particular patient is located.

13. The computer-implemented method of claim 1, further comprising receiving social network activity for the particular patient, wherein the determination that the particular patient failed to perform the at least one task is further based on the social network activity.

14. The computer-implemented method of claim 13, further comprising generating an alert to an emergency contact based on the social network activity.

15. The computer-implemented method of claim 13, further comprising analyzing the social network activity to determine whether a social post includes at least one predetermined keyword or phrase indicating that the particular patient is having a crisis.

16. The computer-implemented method of claim 1, wherein the number of categories comprises at least one of: empiricism, rationalism, humanism, and collectivism.

* * * * *